(12) United States Patent
Jones

(10) Patent No.: US 8,834,908 B2
(45) Date of Patent: *Sep. 16, 2014

(54) PESTICIDAL COMPOSITIONS AND METHODS OF USE THEREOF

(75) Inventor: Allen Jones, Clayton, NC (US)

(73) Assignee: HOMS, LLC, Pittsboro, NC (US)

( * ) Notice: Subject to any disclaimer, the term of this patent is extended or adjusted under 35 U.S.C. 154(b) by 100 days.

This patent is subject to a terminal disclaimer.

(21) Appl. No.: 13/402,248

(22) Filed: Feb. 22, 2012

(65) Prior Publication Data

US 2012/0148653 A1    Jun. 14, 2012

Related U.S. Application Data

(62) Division of application No. 12/698,489, filed on Feb. 2, 2010, now Pat. No. 8,142,801.

(60) Provisional application No. 61/149,114, filed on Feb. 2, 2009.

(51) Int. Cl.
*A01N 25/32* (2006.01)
*A01N 37/02* (2006.01)

(52) U.S. Cl.
CPC .............. *A01N 37/02* (2013.01); *A01N 25/32* (2013.01); *Y10S 424/10* (2013.01); *Y10S 514/875* (2013.01); *Y10S 514/919* (2013.01); *Y10S 514/92* (2013.01); *Y10S 514/938* (2013.01)
USPC .................... 424/406; 424/94.63; 424/94.64; 424/94.66; 424/94.67; 424/45; 424/405; 424/407; 424/725; 424/747; 424/770; 424/DIG. 10; 514/517; 514/549; 514/558; 514/675; 514/703; 514/875; 514/919; 514/920; 514/938; 514/729

(58) Field of Classification Search
None
See application file for complete search history.

(56) References Cited

U.S. PATENT DOCUMENTS

| | | | |
|---|---|---|---|
| 4,721,706 A | 1/1988 | Bessler et al. | |
| 5,174,989 A | 12/1992 | Tanaka et al. | |
| 6,548,085 B1 | 4/2003 | Zobitne et al. | |
| 6,649,579 B2 | 11/2003 | Denton | |
| 6,936,572 B2 * | 8/2005 | Stewart et al. | 504/362 |
| 6,972,132 B1 * | 12/2005 | Kudo et al. | 424/461 |
| 7,019,036 B2 | 3/2006 | Hiromoto | |
| 7,884,037 B2 | 2/2011 | Sirovatka et al. | |
| 8,142,801 B2 | 3/2012 | Jones | |
| 2008/0146444 A1 * | 6/2008 | Fabri et al. | 504/100 |
| 2011/0189251 A1 * | 8/2011 | Roe et al. | 424/413 |

OTHER PUBLICATIONS

Mar. 16, 2011 Office Action in U.S. Appl. No. 12/698,489, issued by Neil S. Levy.
Jun. 29, 2011 Office Action in U.S. Appl. No. 12/698,489, issued by Neil S. Levy.
Dec. 13, 2011 Notice of Allowance in U.S. Appl. No. 12/698,489, issued by Neil S. Levy.

* cited by examiner

*Primary Examiner* — Neil Levy
(74) *Attorney, Agent, or Firm* — Hultquist, PLLC; Steven J. Hultquist; David Bradin

(57) ABSTRACT

A pest-combating composition including sodium lauryl sulfate and one or more of $C_{6-12}$ fatty acids, preferably lauric and/or capric and/or caprylic acid, soy methyl ester, and 2-undecanone, and methods of combating pests utilizing same, are disclosed. The compositions can include a carrier oil such as silicon oil, soy methyl ester, or a vegetable oil, and can be in the form of an emulsion. The composition may be constituted as a spray composition, an aerosol, a lotion, a paste, or another compositional form. Pests that may be usefully combated with such composition include flying insects, including flies, mosquitoes, and wasps, ants, including arthropods such as fire ants, ticks, fleas, cockroaches, silver fish, thrips, gnats, aphids, Japanese beetles, and agricultural and horticultural arthropods and insects including beetles (potato and bean), flea beetles, fleahoppers, squash bugs, slugs, leaf hoppers, harlequin bugs, milk weed bugs, spiders, mites, lice, rodents, and deer.

17 Claims, No Drawings

PESTICIDAL COMPOSITIONS AND METHODS OF USE THEREOF

CROSS-REFERENCE TO RELATED APPLICATION

This application claims priority as a divisional application of U.S. patent application Ser. No. 12/698,489, filed Feb. 2, 2010, which in turn claims priority of U.S. Provisional Patent Application No. 61/149,114 filed Feb. 2, 2009. The disclosures of all such applications are hereby incorporated herein by reference in their respective entireties, for all purposes.

FIELD OF THE INVENTION

The present invention relates to compositions having utility for combating pests, including ants, fire ants, mosquitoes, ticks, and other arthropods and insect species.

DESCRIPTION OF THE RELATED ART

In the field of insecticides and pesticides, as well as insect and pest repellents, much effort has been given to the development of compositions that are "environmentally friendly." Accordingly, there has been a great interest in compositions that are readily biodegradable or otherwise compatible with human and animal use as formulations having little or no toxicity. A limitation associated with developing these types of pesticides is that they tend to be less effective and short residual activity. The pesticides need to be developed with synergistic activity to make them as effective as the toxic chemicals with residual activity.

Pest species include mosquitoes, ticks, fleas, flies, chiggers, lice, mites, roaches, and other pests, including insect, arachnid, and crustacean species that are vectors of human disease-causing agents. Mosquitoes and ticks are of primary interest as disease carriers. Mosquitoes and ticks, for example, carry Lyme disease, encephalitis, and other diseases. Mosquitoes and ticks transmit the widest variety of pathogens out of all blood-sucking arthropods. As a result, there is a great interest in developing pesticidal compositions, as well as repellent compositions. It can be advantageous to kill insects and arthropods in a particular crop locus, in a residential area, and in the transport of foods and other sensitive cargo that can be contaminated by arthropods, and to prevent transporting arthropods between geographic regions, before they can get close enough to humans to transmit disease, and also before they can damage crops. It would be particularly advantageous to kill flying insects with a composition with "knock-down" power, so that the insect can not only be killed at a distance, but prevented from attacking a person after it is hit with an ultimately lethal, but fast-acting pesticidal composition. Current fast acting pesticidal composition are generally restricted to specific uses due to their toxic and environmentally poisonous characteristics. Current toxic pesticides include permethrin and other pyrethroids. It is of primary importance to have a pesticide as effective as these toxic materials, but environmentally sensitive and far less toxic to humans and animals.

It is also of importance, though secondary to pesticidal activity, to have insect repellents that are efficacious for controlling mosquitoes and ticks on animals and human skin, and which is relatively as effective, as repellents based on N,N-diethyl-m-toluamide (DEET).

Although there has been increasing use of various natural ingredients in pest-combating compositions, such natural ingredients typically are utilized in the form of isolates or purified species, rather than being chemically processed to other ingredient forms. This self-imposed limitation on the formulation of so-called "green" products has in many cases limited the chemical efficacy of the compositions for their intended pest-combating usage.

In consequence, the art continues to seek improvements in natural product formulations for combating insects and other pests.

SUMMARY OF THE INVENTION

The present invention relates to pest-combating compositions, and methods of killing and/or repelling pests using the compositions. The compositions are preferably DEET-free and pyrethroid-free.

In one embodiment, the compositions contain as active ingredients, sodium lauryl sulfate and one or more $C_{6-12}$ fatty acids, preferably lauric and/or capric and/or caprylic acid. In one aspect of this embodiment, the compositions further include a carrier. Suitable carriers include silicon oil, soy methyl ester, or vegetable oils such as canola, corn, cotton, palm, rapeseed, safflower, soybean, and sunflower oils, and mixtures thereof, and, more specifically, soybean oil or coconut oil. Soy methyl ester can be preferred among these carriers. The compositions can be in the form of an oil-in-water emulsion, a water-in-oil emulsion, a micelle formulation, a solution, a suspension, a dispersion, and the like. In any of these forms, the formulations can include a propellant, so that they can be aerosolized. Such aerosolized compositions can be used in fumigation applications, such as ship/air cargo or food containment areas. The compositions can also be used as a pesticide treatment prior to transporting items. In one embodiment, the compositions are converted to aerosol compositions by adding nitrogen to the formula, and keeping the contents in a pressurized container, such as a metal can. Nitrogen is an inert additive, and not a green-house gas, and can be preferred over other propellants, such as low molecular weight hydrocarbons. When present, the nitrogen is present in an amount of up to 10 percent, though is typically in the range of about 0.5% by weight of the composition.

The sodium lauryl sulfate is typically present in an amount ranging from about 0.1 to about 10% by weight of the composition, more typically in an amount ranging from 1.0 to about 5% by weight.

In another embodiment, the compositions contain, as active ingredients, a combination of sodium lauryl sulfate and soy methyl ester, without the fatty acids being present.

In either of these embodiments, the compositions can further include 2-undecanone. The presence of 2-undecanone or rue oil further enhances the insecticidal/pesticidal activity of the compositions by reducing time to mortality on specific insects, arachnids, and/or arthropods. In one embodiment, the 2-undecanone is present by virtue of the composition including rue oil (an essential oil extracted from *Ruta graveolens* of the Rutaceae family, also known as garden rue and herbygrass). The presence of 2-undecanone or rue oil increases the pest repellency to insects, arthropods and animals such as rodents and deer In a third embodiment, the compositions contain, as active ingredients, a combination of sodium lauryl sulfate and 2-undecanone or rue oil. In this embodiment, the compositions can further include fatty acids, a vegetable oil such as soybean oil or coconut oil, soy methyl ester, and/or silicon oil. The oils can be part of a water-in-oil or oil-in-water emulsion.

In a fourth embodiment, the formulation does not include oil, and is therefore not an emulsion or micelle. For example, an aqueous solution can be prepared including between about 0.5% and 10% sodium lauryl sulfate, one or more fatty acids such as lauric, capric or caprylic acid in an amount ranging from 0.5% and 20%, a fatty acid salt, such as potassium oleate, in an amount ranging from 0.25% and 5%, a humectant such as glycerin in an amount ranging from 0.5% and 0%, glycerol monostearate or other fatty acid mono-glycerides in an amount ranging from 0.5% and 20%, with the balance being water, all amounts measured w/w. 2-undecanone can also be added to this formula to increase activity and repellency at 0.1% to 5%. In addition, the enzyme Subtilisin can be added to enhance insecticidal activity to this formula from 0.1% to 10%, and can also help control allergens, such as those produced by pests.

Also, the compositions can include a fragrance such as menthol, citral, lemongrass oil, and/or cedar oil, to make the scent more acceptable. Menthol can be preferred in the shampoo version for humans and animals to control lice, ticks and mites as it also relieves the itch that is frequently associated with pest infestation.

The compositions can be formulated for application to a human or animal, for example, in the form of sprays, lotions, or liquid compositions, and used, for example, as pesticides, and, in some embodiments, as insect repellents. In insecticidal uses, the compositions can be used in shampoos, and the like, to kill lice, ticks, fleas, and mites, in both animals and humans.

Alternatively, the compositions can be applied to an article or a region/locus. Typical application rates when applied to a region/locus are in the range of about 0.01 oz/square inch.

The compositions can be combined with an insect attractant and/or a feeding stimulant, particularly in bait applications. The insect attractant and/or feeding stimulant are preferably naturally-occurring insect attractants or feeding stimulants. Representative examples of insect attractants include insect pheromones, and, for mosquitoes, human sweat or its components, or carbon dioxide. Representative feeding stimulants include cucurbitacins, corn oil, peanut oil, and the like. In these embodiments, the compositions attract the insects, and then kill them.

In one embodiment, the compositions are combined with a thixotropic agent. In this embodiment, mechanical agitation, such as that which occurs when the composition is sprayed, liquefies the composition and allows it to be applied in aerosol form. When the mechanical agitation is stopped, the compositions then return to their original state, for example, a gel, so that they can remain attached to where they are applied. The use of a thixotropic agent can enable the formulations to be prepared without using any oil, and enables the active components to stick on plant surfaces, and protect the plants from insect damage.

In some embodiments, the formulations have insect repellent or insecticidal properties, but are not phytotoxic. Examples of plants that can be treated include shrubs, vegetable gardens, grasses, and trees, such as fruit trees. As such, the formulations can be used as insecticides, and to prevent insect damage on lawns and in agricultural and horticultural applications, as well as residential and commercial applications.

Representative insects that can be killed using the compositions described herein include ants, cockroaches, beetles (potato and bean), flea beetles, fleahoppers, squash bugs, stink bugs, aphids, thrips, slugs, leaf hoppers, harlequin bugs and milk weed bugs. Representative insects that can be repelled using the compositions described herein include caterpillars, maggots, moths, and grasshoppers. Rodents and deer were also repelled with some formulations.

The lack of phytotoxicity, lack of oils, and the use of a thixotropic agent allows the composition to be used primarily as an insecticide and insect damage preventer for lawns, agricultural and horticultural applications, though it is also useful for residential and commercial applications. The thixotropic agent enables the actives to stick on the surface of a plant protecting it from insects without the use of an oil. This formula is also able to be certified organic.

Another aspect of the invention relates to a packaged insect repellent, comprising a container holding the pesticidal composition described herein.

A still further aspect of the invention relates to a method of combating pests, at a locus containing or susceptible to the presence of same, such method including applying to at least a portion of such locus a pesticidal composition as described herein.

In another embodiment, the compositions can be used as a repellent to rodents and deer, particularly when the compositions include undecanone or rue oil, which can find particular application in agricultural and residential applications.

Other aspects, features and embodiments of the invention will be more fully apparent from the ensuing disclosure and appended claims.

DETAILED DESCRIPTION

The present invention is based on the discovery that sodium lauryl sulfate and $C_{6-12}$ fatty acids, preferably lauric, capric and/or caprylic acids, are unexpectedly and highly effective as pest-combating active ingredients in the pest control formulations. The present invention is also based on the discovery that sodium lauryl sulfate and soy methyl ester and/or 2-undecanone, with or without $C_{6-12}$ fatty acids such as lauric, capric and/or caprylic acids, are unexpectedly and highly effective as pest-combating active ingredients. The compositions of the present inventions, and methods of use thereof, are described in detail below.

I. Pesticidal Compositions

Main Active Agents

In one embodiment, the pesticidal compositions described herein include sodium lauryl sulfate and one or more $C_{6-12}$ fatty acids, preferably lauric and/or capric and/or caprylic acids.

In another embodiment, the pesticidal compositions described herein include sodium lauryl sulfate and/or soy methyl ester (the soy methyl ester can optionally be replaced or combined with any transesterified ester) in combination with sodium lauryl sulfate and/or 2-undecanone or rue oil (which includes a significant amount of 2-undecanone).

Combinations of sodium lauryl sulfate and two or more of these active agents are intended to be within the scope of the invention.

In some embodiments, the compositions further include an enzyme, which is preferably a protease.

Sodium Lauryl Sulfate

Sodium lauryl sulfate is an emulsifier, an also has insecticidal properties. Accordingly, when the compositions include sodium lauryl sulfate, water, and a carrier oil, such as silicon oil, a vegetable oil, mineral oil, or soy methyl ester, the sodium lauryl sulfate can serve as the emulsifier. The concentration of sodium lauryl sulfate in the compositions described herein is typically in the range of about 0.1 to about 10 percent by weight of the composition, more typically in the range of about 1.0 to about 5 percent by weight of the composition.

Fatty Acids

Fatty Acids give the formulation quick insecticidal activity. The fatty acids are typically in the range of $C_{6-12}$ fatty acids, and, preferably, include lauric and/or capric and/or caprylic acids. One representative fatty acid formulation is C810 (formerly known as LC810 in CIP2 from Peter Cremer). C810 is supplied by Univar and manufactured by Proctor & Gamble. It is a blend primarily of Capric (octanoic) Acid & Caprylic (Decanoic) Acid.

Undecanone

In some embodiments, the compositions include isolated 2-undecanone or rue oil, the main constituent of which is 2-undecanone. 2-Undecanone also gives the formulation quick insecticidal activity. In some embodiments, the 2-undecanone functions as an insect repellent, rather than an insecticide. For example, compositions containing 2-undecanone exhibit repellency against mosquitoes, ticks, cockroaches, thrips, deer fly, gnats, aphids, and the like. In other embodiments, the 2-undecanone functions or rue oil to enhance the pesticidal effectiveness of the compositions. The 2-undecanone enhances the pest repellency of the compositions to repel animals such as rodents and deer.

Due to the volatility of 2-undecanone, it can be desirable to formulate the composition containing such ingredient with a sticking agent, so that the 2-undecanone in the composition persists at the point of application, to extend the duration of active repellency of the composition.

Soy Methyl Ester

Soy methyl ester (also referred to herein as "SME") is an optional active agent, and can serve a dual role. It can serve not only as an active agent, enhancing the pesticidal activity and insect repellency of the compositions, but also as a base for an emulsion incorporating the composition. SME also is a solvent to 2-undecanone, and can provide stable emulsions and control the rate of volatile 2-undecanone release over time.

As used herein, the term "soy methyl ester" refers to methyl ester(s) of fatty acids or oleochemicals of soybean oil, and sometimes is referred to as soybean oil methyl ester or as soybean methyl ester. Soy methyl esters are readily produced by subjecting fatty acids and oleochemicals of soybean oil to transesterification chemical reaction, e.g., a base-catalyzed transesterification of soybean oil. Soy methyl esters of widely varying types are usefully employed in the practice of the invention. One particularly preferred soy methyl ester comprises a mixture of $C_{16}$-$C_{18}$ saturated and $C_{18}$ unsaturated methyl esters, identified by Chemical Abstracts Registry Number (CAS#) 67762-38-3.

Soy methyl esters usefully employed in compositions of the present invention are readily commercially available, e.g., under the brand name "Enviro-Saver" from Columbus Foods Company (Chicago, Ill.), under the brand name "Ecoline Soya Methyl Esters" from Cortec Corporation (St. Paul, Minn.), and otherwise as fatty acid methyl ester from Cargill Industrial Oils & Lubricants (Minneapolis, Minn.), as methyl soyate from Cognis Corporation (Cincinnati, Ohio), and as soy methyl esters from Vertec BioSolvents, Inc. (Downers Grove, Ill.), Lambent Technologies Corporation (Gurnee, Ill.), soy-based fatty acid esters from Chemol Company, Inc. (Greensboro, N.C.), SoyGold 1000 from Ag Environmental Products (Omaha, Nebr.), and Steposol SB-D and Stepasol SB-W soy methyl esters from Stepan Company (Northfield, Ill.).

The soy methyl ester can be used at any suitable concentration in the compositions of the invention. Preferably, the soy methyl ester has a concentration in the composition of from about 2% to about 15% by weight, based on the total weight of the composition. More preferably, the soy methyl ester has a composition concentration in a range of from about 2.4% to about 12% by weight, based on total weight of the composition. Most preferably, the soy methyl ester has a concentration in the composition in a range of from about 3 to about 10% by weight, based on total weight of the composition.

In place of, or in addition to, the soy methyl ester, other transesterified triglycerides can be used, including methyl and other $C_{1-10}$ alkyl esters of other triglycerides, and $C_{2-10}$ alkyl esters of the fatty acids found in soybean oil.

Feeding Stimulants/Attractants

The efficacy of the compositions can, in some embodiments, be enhanced by using a feeding stimulant and/or attractant. This is particularly true where the compositions are used in bait applications. The use of feeding stimulants and attractants allow one to apply the insecticidal compositions at a reduced rate over a given locus, such as a crop locus.

Bait stations typically deliver an insecticide through a sealed plastic or metal chamber that insects enter. This gives bait stations the advantage of decreasing both the amount of insecticide used and the likelihood of exposure to it. Where, as here, the compositions typically include essentially harmless components, the main use for bait stations is to lure the insects away from areas of concern, such as where crops are growing, children are present, or food is prepared or stored.

Ideally, the feeding stimulants and/or attractants are naturally-occurring substances.

For termites, one type of feeding stimulant is sitosterol. Sitosterol is known to increase feeding or induce phagostimulatory responses by all termite species. Termite species known to show increased feeding on cellulosic baits containing sitosterol include *Coptotermes formosanus, Reticulitermes tibialis, Reticulitermes flavipes*, and *Reticulitermes virginicus*. Sitosterol can also be used in connection with other important pest species of termites, in particular: *Reticulitermes hesperus, Reticulitermes hageni*, and *Heterotermes* species.

Representative examples of insect attractants for mosquitoes include human sweat or its components, and carbon dioxide.

Representative feeding stimulants for fire ants include corn oil, peanut oil, and the like.

Cucurbitacin-based feeding stimulants can be used to control insects in the *Diabrotica* family, including adult western corn rootworms, *Diabrotica virgifera virgifera*. Representative feeding stimulants for *Diabrotica* include cucurbitacin The green mirid, *Creontiades dilutus* is a true bug (order Hemiptera, suborder Heteroptera), characterized by piercing and sucking mouthparts. The green mirid is a pest of cotton, and is found in other crops, such as lucerne, potatoes, soy beans, stone fruits, sunflower and grapes. A mixture of hexyl hexanoate and (E)-2-hexenyl hexanoate is an insect pheromone for the green mirid.

Additional feeding stimulants and attractants, where the term attractant is intended to include pheromones and kairomones, include:

Z-5-decenyl acetate, dodecanyl acetate, Z-7-dodecenl acetate, E-7-dodecenyl acetate, Z-8-dodecenyl acetate, E-8-dodecenyl acetate, Z-9-dodecenyl acetate, E-9-dodecenylacetate, E-10-dodecenyl acetate, 11-dodecenyl acetate, Z-9,11-dodecadienyl acetate, E-9,11-dodecadienyl acetate, Z-11-tridecenyl acetate, E-1-tridecenyl acetate, tetradecenyl acetate, E-7-tetradecenyl acetate, Z-8-tetradecenyl acetate, E-8-tetradecenyl acetate, Z-9-tetradecenyl acetate, E-9-tetradecenyl acetate, Z-10-tetradecenyl acetate, E-10-tetradecenyl acetate, Z-11-tetradecenyl acetate, E-11-tetradecenyl acetate, Z-12-pentadecenyl acetate, E-12-pentadecenyl acetate, hexadecenyl acetate, Z-7-hexadecenyl acetate, Z-11-hexadecenyl acetate, E-11-hexadecenyl acetate, octadecanyl acetate, E,Z-7,9-dodecadienyl acetate, Z,E-7,9-dodecadienyl acetate, E,E-7,9-dodecadienyl acetate, Z,Z-7,9-dodecadienyl acetate, E,E-8,10-dodecadienyl acetate, E,Z-9,12-dodecadienyl acetate, E,Z-4,7-tridecadienyl acetate, 4-methoxy-cinnamaldehyde, .beta.-ionone, estragole, eugenol, indole, 8-methyl-2-decyl propanoate, E,E-9,11-tetradecadienyl acetate, Z,Z-9,12-tetradecadienyl acetate, Z,Z-7,11-hexadecadienyl acetate, E,Z-7,11-hexadecadienyl acetate, Z,E-7,11-hexadecadienyl acetate, E,E-7,11-hexadecadienyl acetate, Z,E-3,13-octadecadienyl acetate, E,Z-3,13-octadecadienyl acetate, E,E-3,13-octadecadienyl acetate, ethanol, hexanol, heptanol, octanol, decanol, Z-6-nonenol, E-6-nonenol, dodecanol, 11-dodecenol, Z-7-dodecenol, E-7-dodecenol, Z-8-dodecenol, E-8-dodecenol, E-9-dodecenol, Z-9-dodecenol, E-9,11-dodecadienol, Z-9,11-dodecadienol, Z,E-5,7-dodecadienol, E,E-5,7-dodecadienol, E,E-8,10-dodecadienol, E,Z-8,10-dodecadienol, Z,Z-8,10-dodecadienol, Z,E-8,10-dodecadienol, E,Z-7,9-dodecadienol, Z,Z-7,9-dodecadienol, E-5-tetradecenol, Z-8-tetradecenol, Z-9-tetradecenol, E-9-tetradecenol, Z-10-tetradecenol, Z-11-tetradecenol, E-11-tetradecenol, Z-11-hexadecenol, Z,E-9,11-tetradecadienol, Z,E-9,12-tetradecadienol, Z,Z-9,12-tetradecadienol, Z,Z-10,12-tetradecadienol, Z,Z-7,11-hexadecadienol, Z,E-7,11-hexadecadienol, (E)-14-methyl-8-hexadec-en-1-ol, (Z)-14-methyl-8-hexadecen-1-ol, E,E-10,12-hexadecadienol, E,Z-10,12-hexadecadienol, dodecanal, Z-9-dodecenal, tetradecanal, Z-7-tetradecenal, Z-9-tetradecenal, Z-11-tetradecenal, E-11-tetradecenal, E-11,13-tetradecadienal, E,E-8,10-tetradecadienal, Z,E-9,11-tetradecadienal, Z,E-9,12-tetradecadienal, hexadecanal, Z-8-hexadecenal, Z-9-hexadecenal, Z-10-hexadecenal, E-10-hexadecenal, Z-11-hexadecenal, E-11-hexadecenal, Z-12-hexadecenal, Z-13-hexadecenal, (Z)-14-methyl-8-hexadecenal, (E)-14-methyl-8-hexadecenal, Z,Z-7,11-hexadecadienal, Z,E-7,11-hexadecadienal, Z,E-9,11-hexadecadienal-, E,E-10,12-hexadecadienal, E,Z-10,12-hexadecadienal, Z,E-10,12-hexadecadienal, Z,Z-10,12-hexadecadienal, Z,Z-11,13-hexadecadienal, octadecanal, Z-11-octadecenal, E-13-oxtadecenal, Z-13-octadecenal, Z-5-decenyl-3-methyl-butanoate Disparlure: (+) cis-7,8-epoxy-2-methyloctadecane, Seudenol: 3-methyl-2-cyclohexen-1-ol, sulcatol: -methyl-5-hepten-2-ol, Ipsenol: 2-methyl-6-methylene-7-octen-1-ol, Ipsdienol: 2-methyl-6-methylene-2,7-octadien-4-ol, Grandlure I: cis-2-isopropenyl-1-methyl-cyclobutanethanol, Grandlure II: Z-3, 3-dimethyl-1-cyclohexanethanol, Grandlure III: Z-3,3-dimethyl-1-cyclohexaneacetaldehyde, Grandlure IV: E-3,3-dimethyl-1-cyclohexaneacetaldehyde, cis-2-verbenol: cis-4,6,6-trimethylbicyclo[3,1,1]hept-3-en-2-ol cucurbitacin, 2-methyl-3-buten-2-ol, 4-methyl-3-heptanol, cucurbitacin, 2-methyl-3-buten-2-ol, 4-methyl-3-heptanol, alpha-pinene: 2,6,6-trimethylbicyclo[3,1,1]hept-2-ene, alpha-caryophyllene: 4,11,11-trimethyl-8-methylenebicyclo[7,2,0]undecane, Z-9-tricosene, alpha-multistriatin 2(2-endo, 4-endo)-5-ethyl-2,4-dimethyl-6,8-dioxabicyclo[3,2,1]octane, methyleugenol: 1,2-dimethoxy-4-(2-propenyl)phenol, Lineatin: 3,3,7-trimethyl-2,9-dioxatricyclo[3,3,1,0]nonane, Chalcogran: 2-ethyl-1,6-dioxaspiro[4,4]nonane, Frontalin: 1,5-Dimethyl-6,8-dioxabicyclo[3,2,1]octane, endo-Brevicomin: endo-7-ethyl-5-methyl-6,8-dioxabicyclo[3-,2,1]octan, exo-brevicomin: exo-7-ethyl-5-methyl-6,8-dioxabicyclo[3,2,1]octane, (Z)-5-(1-decenyl)dihydro-2-(3H)-furanone, Farnesol 3,7-11-trimethyl-2,6,10-dodecatrien-1-ol, Nerolidol 3,7-,11-trimethyl-1,6,10-dodecatrien-3-ol, 3-methyl, 6-(1-methyl ethenyl)-9-decen-1-ol acetate, (Z)-3-methyl-6-(1-methylethenyl)-3,9-decadien-1-ol acetate, (E)-3,9-methyl-6-(1-methylethenyl)-5,8-decadien-1-ol-acetate, 3-methylene-7-methyl-octen-1-ol propionate, (Z)-3,7-dimethyl-2,7-octadien-1-ol propionate, (Z)-3,9-dimethyl-6-(1-methylethenyl)-3,9-decadien-1-ol propionate.

Optional Additional Components

For example, the additional ingredients may include fillers, dispersants, water or other solvent medium or media, surfactants, suspension agents, sticking agents, stabilizers, preservatives, dyes, pigments, masking agents, emollients, excipients, post-application detection agents, and additional active ingredients. For example, the composition may be formulated with a sunscreen and/or sunblocking agent.

Such additional active ingredients may include, for example, additional pest-combating ingredients, such as repellents and/or cidal agents. By way of example, the compositions may be formulated with an insect repellent ingredient. The repellents/cidal agents are preferably, but need not be, naturally-occurring.

Thickening Agents/Sticking Agents

Representative sticking agents include, but are not limited to, polyvinyl acetates, polyvinyl alcohols, dextrins, sugars and vegetable oils.

Thickeners can also be used. Examples of suitable thickeners include organic polymers, such as partially or fully neutralized polyacrylic acids (Carbopol®, polyethylene glycols (Polyox®), polyvinyl alcohols and non-ionically or ionically modified celluloses (Tylose®), xanthan-based thixotropic thickeners (Kelzan®), and also inorganic disperse thickeners, such as precipitated or pyrogenic silicas, kaolins, bentonites and aluminum/silicon mixed oxides. Potassium oleate is another thixotropic agent, and is present in the formulation described in Example 4 below. In some embodiments, the formulation includes sodium lauryl sulfate, fatty acids and thixotropic agents, but does not include an oil.

Naturally-Occurring Repellent/Cidal Agents

In one embodiment, the additional repellent or cidal agents are essential oils or plant extracts.

Plant Extracts

Representative plant extracts (botanical insecticides) include:

Neem, azadirachtin, limonene, capsaicin, pyrethrum and pyrethrins, garlic,

Neem is made from extracts of Neem tree seeds, and is used to control a wide variety of insects including leafminers, whiteflies, thrips, caterpillars, aphids, mealybugs, spider mites, scale crawlers, and beetles. Azadirachtin is the active ingredient in neem extracts. Neem tends to not produce a quick knockdown or kill, but stops insect feeding.

Limonene (also known as d-Limonene) is produced from citrus oils extracted from oranges and other citrus fruit peels. It is used as a contact insecticide against ants, roaches, palmetto bugs, fleas, silverfish, fire ants, and many other insects. Limonene is the active ingredient in Ortho Home Defense Indoor Insect Killer, Concern Citrus Home Pest Control, and Citrex Fire Ant Killer.

Capsaicin is the material that makes chili peppers hot, and is used to control (mainly to repel) aphids, spider mites, thrips, whitefly, lace bugs, leafhoppers, and other pests.

Pyrethrum is made from the finely powdered flowers of a species of daisy. The word pyrethrum is the name for the crude flower dust itself, and the term pyrethrins refers to the insecticidal compounds that are extracted from pyrethrum. Pyrethroids are not botanical insecticides, but synthetic pesticides that are very similar in structure to the pyrethrins.

Pyrethrum is a contact insecticide and must be applied directly to the insect to be effective. Pyrethrum rapidly paralyzes pests, but may not kill them. Pyrethrum and pyrethrins are often formulated with another insecticide to ensure that paralyzed insects do not recover.

Essential Oils

There are a number of essential oils or components of essential oils with insecticidal properties. Examples include the oils of cedar, cinnamon, citronella, citrus, clove, eugenol (a component of clove oil), garlic, mints, such as peppermint and spearmint, rosemary, and several others. As insecticides, these work most commonly as contact killing agents only, so re-treatment may be needed. Most essential oils used as pesticides work by disrupting an insect neurotransmitter that is not present in people, pets, or other vertebrates.

Peppermint oil, one example of an essential oil with cidal properties, is particularly active against ants, roaches, waterbugs, silverfish, crickets, spiders and centipedes.

Fragrances

The compositions can include one or more fragrances, which, in some embodiments, are essential oils such as those described above. Although it can be preferred to use natural components, the fragrances can include non-naturally occurring chemicals. In some embodiments, the fragrance can also impart a beneficial property to the compositions, for example, where menthol is used as both a fragrance and an anti-itch component when the compositions are applied to human or animal skin.

Representative fragrances include floral or plant oil fragrances such as citrus, clove, eucalyptus, wintergreen, rosemary, citronella or cinnamon oil, which also possesses pesticidal and antimicrobial properties.

A wide variety of chemicals are known for perfumery, such as aldehydes, ketones, esters, alcohols, terpenes, and the like. Most conventional fragrance materials are volatile essential oils.

Natural fragrances include naturally derived oils such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like. Natural perfumes include the extracts of blossoms, stems and leaves, fruits, fruit peel, roots, woods, herbs and grasses, needles and branches, resins and balsams. Other suitable perfume oils are essential oils of relatively low volatility which are mostly used as aroma components. Examples include sage oil, chamomile oil, clove oil, melissa oil, mint oil, cinnamon leaf oil, lime-blossom oil, juniper berry oil, vetivert oil, olibanum oil, galbanum oil, ladanum oil and lavendin oil.

Typical synthetic perfume compounds are products of the ester, ether, aldehyde, ketone, alcohol and hydrocarbon type. Examples of perfume compounds of the ester type are benzyl acetate, p-tert-butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams.

Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

Non-Naturally Occurring Repellent or Cidal Agents

While it can be preferred in some embodiments for the compositions to be capable of being organically certified, as including only natural ingredients, in another embodiment, the additional repellent or cidal agents are non-naturally occurring substances. Representative repellent and cidal agents include compounds or compositions that are used as acaricides, insecticides, insecticide synergists, ixodicides, nematicides, and molluscicides. Chemical classes of insecticides include 2-dimethylaminopropane-1,3-dithiol, 2-dimethylaminopropane-1,3-dithiol analogs, amidines, arylpyrroles, avermectin, benzoylureas, carbamates, carbamoyltriazoles, cyclodienes, diacylhydrazines, dinitrophenols, fiprole, METI, neonicotinoids, non-ester pyrethroids, organochlorines, organophosphates, oxadiazines, oximes, carbamates, pyrethroids, and spinosyns. Suitable insecticides include 1,1-bis(4-chlorophenyl)-2-ethoxyethanol, 1,1-dichloro-1-nitroethane, 1,1-dichloro-2,2-bis(4-ethylphenyl)ethane, 1,2-dichloropropane with 1,3-dichloropropene, 1-bromo-2-chloroethane, 2-(1,3-dithiolan-2-yl)phenyl dimethylcarbamate, 2-(2-butoxyethoxy)ethyl thiocyanate, 2-(4,5-dimethyl-1,3-dioxolan-2-yl)phenyl methylcarbamate, 2-(4-chloro-3,5-xylyloxy)ethanol, 2,2,2-trichloro-1-(3,4-dichlorophenyl)ethyl acetate, 2,2-dichlorovinyl 2-ethylsulfinylethyl methyl phosphate, 2,4-dichlorophenyl benzenesulfonate, 2-chlorovinyl diethyl phosphate, 2-isovalerylindan-1,3-dione, 2-methyl(prop-2-ynyl)aminophenyl methylcarbamate, 2-thiocyanatoethyl laurate, 3-bromo-1-chloroprop-1-ene, 3-methyl-1-phenylpyrazol-5-yl dimethylcarbamate, 4-chlorophenyl phenyl sulfone, 4-methyl(prop-2-ynyl)amino-3,5-xylyl methylcarbamate, 4-methylnonan-5-ol with 4-methylnonan-5-one, 5,5-dimethyl-3-oxocyclohex-1-enyl dimethylcarbamate, 6-methylhept-2-en-4-ol, abamectin, acephate acequinocyl, acrinathrin, alanycarb, aldicarb, aldoxycarb, aldrin, allethrin [(1R)-isomers], allyxycarb, alpha-cypermethrin, amidithion, amidothioate, aminocarb, amiton; amiton hydrogen oxalate, amitraz, anabasine, aramite, athidathion, azadirachtin, azamethiphos, azinphos-ethyl, azinphos-methyl, azocyclotin, azothoate, barium polysulfide, Bayer 22/190, Bayer 22408, bendiocarb, benfuracarb, bensultap, benzoximate, beta-cyfluthrin, beta-cypermethrin, bifenazate, bifenthrin, binapacryl, biopermethrin, bis(2-chloroethyl)ether, bistrifluoron, bromfenvinfos, bromocyclen, bromophos, bromophos-ethyl, bromopropylate, bufencarb, buprofezin, butacarb, butathiofos, butocarboxim, butonate, butoxycarboxim, cadusafos, calcium polysulfide, camphechlor, carbanolate, carbaryl, carbofuran, carbophenothion, carbosulfan, cartap hydrochloride, CGA 50 439, chinomethionat, chlorbenside, chlorbicyclen, chlordane, chlordecone, chlordimeform; chlordimeform hydrochloride, chlorethoxyfos, chlorfenapyr, chlorfenethol, chlorfenson, chlorfensulphide, chlorfluazuron, chlormephos, chloro-benzilate, chloromebuform, chloropropylate, chlorphoxim, chlorprazophos, chlorpyrifos, chlorpyrifos-methyl, chlorthiophos, chromafenozide, cloetho-carb, clofentezine, clothianidin, codlemone, coumaphos, coumithoate, crotoxyphos, crufomate, cryolite, CS 708, cyanofenphos, cyanophos, cyanthoate, cycloprothrin, cyfluthrin, cyhalothrin, cyhexatin, cypermethrin, cyphenothrin [(1R)-trans-isomers], cyromazine, DAEP, dazomet, DCPM, DDT, decarbofuran, deltamethrin, demephion; demephion-O; demephion-S, demeton; demeton-O; demeton-S, demeton-S-methyl, demeton-S-methylsulphon, diafenthiuron, dialifos, diazinon, dicapthon, dichlorvos, dicofol, dicrotophos, dicyclanil, dieldrin, dienochlor, diethyl 5-methyl-pyrazol-3-yl phosphate, diflubenzuron, dimefox, dimethoate, dimethrin, dimethylvinphos, dimetilan, dinex; dinex-diclexine, dinobuton, dinocap, dinocton, dinopenton, dinoprop, dinosulfon, dinotefuran, dinoterbon, dioxabenzofos, dioxacarb, dioxathion, diphenyl sulfone, disulfoton, dithicrofos, DNOC, dodec-8-enyl acetate, dofenapyn, DSP, EI 1642, emam ectin benzoate, EMPC, empenthrin [(EZ)-(1R)-isomers], endosulfan, endothion, endrin, ENT 8184, EPBP, EPN, esfenvalerate, ethiofencarb, ethion, ethiprole, ethoate-methyl, ethoprophos, etofenprox, etoxazole, etrimfos, famphur, fenazaflor, fenazaquin, fenbutatin oxide, fenchlorphos, fenethacarb, fenfluthrin, fenitrothion, fenobucarb, fenothio-carb, fenoxacrim, fenoxycarb, fenpirithrin, fenpropathrin, fenpyroximate, fenson, fensulfothion, fenthion, fentrifanil, fenvalerate, fipronil, flonicamid, fluacrypyrim, flubenzimine, flucofuron, flucycloxuron, flucythrinate, fluenetil, flufenoxuron, flufenprox, flumethrin, fluorbenside, fluvalinate, FMC 1137, fonofos, formetanate, formothion, formparanate, fosmethilan, fospirate, fosthiazate, fosthietan, furathiocarb, furethrin, gamma-cyhalo-thrin, gamma-HCH, glyodin, GY-81, halfenprox, halofenozide, heptachlor, heptenophos, hexadecyl cyclopropanecarboxylate, hexaflumuron, hexythiazox, hydramethylnon, hydroprene, hyquincarb, imidacloprid, imiprothrin, indoxacarb, iprobenfos, IPSP, isazofos, isobenzan, isodrin, isofenphos, isolane, isoprocarb, isopropyl O-(methoxyaminothio-phosphoryl)salicylate, isothioate, isoxathion, jodfenphos, kelevan, kinoprene, lambda-cyhalothrin, leptophos, lirimfos, lufenuron, lythidathion, m-cumenyl methylcarbamate, malathion, malonoben, mazidox, MB-599, mecarbam, mecarphon, menazon, mephosfolan, mercurous chloride, mesulfenfos, metam, methacrifos, methamidophos, methanesulfonyl fluoride, methidathion, methiocarb, methocrotophos, methomyl, methoprene, methoquin-butyl, methothrin, methoxychlor, methoxyfenozide, methyl isothiocyanate, metolcarb, metoxadiazone, mevinphos, mexacarbate, milbemectin, mipafox, mirex, MNFA, monocrotophos, morphothion, naled, naphthalene, nicotine, nifluridide, nitenpyram, nithiazine, nitrilacarb; nitrilacarb 1:1 zinc chloride complex, nornicotine, novaluron, noviflumuron, O,O,O'O'-tetrapropyl dithiopyrophosphate, O,O-diethyl O-4-methyl-2-oxo-2H-chromen-7-yl phosphorothioate, O,O-diethyl O-6-methyl-2-propylpyrimidin-4-yl phosphorothioate, O-2,5-dichloro-4-iodophenyl O-ethyl ethylphosphonothioate, oleic acid (fatty acids), omethoate, oxabetrinil, oxamyl, oxydemeton-methyl, oxydeprofos, oxydisulfoton, parathion, parathion-methyl, pentachlorophenol, permethrin, petroleum oils, phenkapton, phenothrin [(1R)-trans-isomer], phenthoate, phorate, phosalone, phosfolan, phosmet, phosnichlor, phosphamidon, phosphine, phoxim, phoxim-methyl, piperonyl butoxide, pirimetaphos, pirimicarb, pirimiphos-ethyl, pirimiphos-methyl, polychlorodicyclopentadiene isomers, polynactins, prallethrin, primidophos, proclonol, profenofos, promacyl, promecarb, propaphos, propargite, propetamphos, propoxur, prothidathion, prothiofos, prothoate, pymetrozine, pyraclofos, pyresmethrin, pyrethrins (pyrethrum), pyridaben, pyridalyl, pyridaphenthion, pyrimidifen, pyrimitate, pyriproxyfen, quinalphos, quinalphos-methyl, quinothion, quintiofos, R-1492, RA-17, resmethrin, rotenone, RU-15525, RU 25475, S421, sabadilla, schradan, silafluofen, SN 72129, sodium fluoride, sodium hexafluorosilicate, sodium selenate, sophamide, spinosad, spirodiclofen, spiromesifen, spirotetramat (BYI8330), SSI-121, sulcofuron-sodium, sulfluramid, sulfosulfuron, sulfotep, sulfur, sulprofos, SZI-12 1, taroils, tazimcarb, TDE, tebufenozide, tebufenpyrad, tebupirimfos, teflubenzuron, tefluthrin, temephos, TEPP, terallethrin, terbufos, tetrachlorvinphos, tetradifon, tetramethrin, tetramethrin [(1R)-isomers], tetrasul, theta-cypermethrin, thiacloprid, thiamethoxam, thicrofos, thiocarboxime, thiocyclam, thiodicarb, thiofanox, thiometon, thionazin, thioquinox, thiosultap-sodium, tolfenpyrad, tralomethrin, transfluthrin, transpermethrin, triamiphos, triarathene, triazamate, triazophos, trichlorfon, trichloronat, trifenofos, triflumuron, trimedlure, trimethacarb, vamidothion, XMC, xylylcarb, zeta-cypermethrin, zolaprofos, and ZXI 8901.

Pigments and Dyes

Suitable colorants include pigments and dyes known in the art. Both natural and synthetic inorganic pigments can be used formulations described herein. Suitable natural inorganic pigments include natural oxides, hydroxides, sulfides, sulfates, silicates, and carbonates of many mineral elements (e.g., iron, magnesium, potassium, aluminum, and copper) as well as mixtures thereof. Red earths, yellow earths, green earths, lapis lazuli, azurite, malachite, other traditional earth colors, and mixtures thereof have been the main sources of natural inorganic pigments. Suitable synthetic inorganic pigments include ferric ammonium ferrocyanide, iron oxide, iron oxide yellow, iron oxide brown, iron oxide orange, iron oxide red, iron oxide black, iron blue, cobalt green, cobalt blue, zinc oxide, zinc sulfide, chrome titanium oxide (Pigment White 6), chromium oxide green (anhydrous), hydrated chrome oxide green, Prussian green, cyanine blue, manganese blue, manganese violet, titanium dioxide, and mixtures thereof. Furthermore, synthetic inorganic pigments made of oxide-coated micas, which may be either titanium dioxide or iron oxide coated micas, can also be used in this invention. Organic pigments in this invention include (using Colour Index names) Pigment Blue 1, Pigment Blue 15, Pigment Blue 15:1, Pigment Blue 15:3, Pigment Blue 15:4, Pigment Blue 61, Pigment Blue 62, Pigment Green 7, Pigment Green 36, Pigment Orange 5, Pigment Orange 13, Pigment Orange 16, Pigment Orange 34, Pigment Orange 36, Pigment Orange 46, Pigment Red 2, Pigment Red 3, Pigment Red 4, Pigment Red 12, Pigment Red 17, Pigment Red 22, Pigment Red 23, Pigment Red 38, Pigment Red 48:1, Pigment Red 48:2, Pigment Red 48:3, Pigment Red 48:4, Pigment Red 49:1, Pigment Red 49:2, Pigment Red 52:1, Pigment Red 53:1, Pigment Red 57, Pigment Red 57:1, Pigment Red 60:1, Pigment Red 63:1, Pigment Red 81, Pigment Red 81:3, Pigment Red 90, Pigment Red 112, Pigment Red 169, Pigment Red 170, Pigment Red 202, Pigment Red 210, Pigment Violet 1, Pigment Violet 3, Pigment Violet 19, Pigment Violet 23, Pigment Violet 27, Pigment Violet 29, Pigment Yellow 1, Pigment Yellow 3, Pigment Yellow 12, Pigment Yellow 13, Pigment Yellow 14, Pigment Yellow 17, Pigment Yellow 62, Pigment Yellow 65, Pigment Yellow 73, Pigment Yellow 74, Pigment Yellow 75, Pigment Yellow 83, Pigment Yellow 111, Pigment Yellow 126, Pigment Yellow 168, Pigment Yellow 184, and mixtures thereof. The inorganic and organic pigment can be a dry powder, slurry, or suspension and can be high solids pigments. The solids content of the pigments can range from about 20 to 70%, the optimum range being from 30 to 65%. Either the solids or the slurry can be post-added and stirred in easily with agitation after the SC or SE formulation is made. The amount of the pigment in the formulation is from about 0.1 to 6%, preferably from 0.1 to 2%.

Water-soluble dyes can be used in the formulations without stability problems. Suitable dyes include Acid Black 172, Acid Black 194, Acid Black 210, Acid Blue 1, Acid Blue 7, Acid Blue 9, Acid Blue 93, Acid Blue 93:1, Acid Green 16, Acid Green 25, Acid Orange 10, Acid Red 14, Acid Red 17, Acid Red 18, Acid Red 52, Acid Violet 17, Acid Violet 49, Acid Yellow 23, Acid Yellow 36, Basic Blue 26, Basic Blue 3, Basic Blue 41, Basic Blue 54, Basic Blue 7, Basic Blue 9, Basic Brown 4, Basic Brown 1, Basic Green 1, Basic Green 4, Basic Orange 1, Basic Orange 2, Basic Orange 21, Basic Red 14, Basic Red 15, Basic Red 18, Basic Red 22, Basic Red 46, Basic Red 49, Basic Violet 1, Basic Violet 10, Basic Violet 14, Basic Violet 16, Basic Violet 2, Basic Violet 3, Basic Violet 4, Basic Yellow 11, Basic Yellow 13, Basic Yellow 2, Basic Yellow 21, Basic Yellow 28, Basic Yellow, 9, Basic Yellow 37, Basic Yellow 40, D&C Green 5, D&C Green 6, D&C Green 8, D&C Orange 4, D&C Orange 5, D&C Red 17, D&C Red 21, D&C Red 22, D&C Red 27, D&C Red 28, D&C Red 30, D&C Red 33, D&C Red 34, D&C Red 36, D&C Red 6, D&C Red 7, D&C Red 8, D&C Violet 2, D&C Yellow 10, D&C Yellow 11, D&C Yellow 7, D&C Yellow 8, FD&C Blue 1, FD&C Blue 2, FD&C Green 3, FD&C Red 3, FD&C Red 4, FD&C Red 40, FD&C Yellow 5 (tartrazine), FD&C Yellow 6, and mixtures thereof. The dyes can be post-added and stirred in easily with agitation after the SC or SE formulation is made. The amount of the dye in the formulation is from about 0.01 to 5%, the optimum range being from 0.02 to 2%.

Emulsifiers/Surfactants

Surfactants can be of the emulsifying or wetting type and can be ionic or nonionic. Representative surfactants include alkali metal, alkaline earth metal and ammonium salts of alkylsulfonic, phenylsulfonic or naphthalenesulfonic acids; polycondensates of ethylene oxide with fatty alcohols or fatty acids or fatty amines or substituted phenols (particularly alkylphenols or arylphenols); ester-salts of sulfosuccinic acids; taurine derivatives, such as alkyl taurates; phosphoric esters; or esters of alcohols or polyoxyethylated phenols.

If a surfactant is used, it is preferential to use a nonionic surfactant. However, the nonionic surfactant is used in an effective amount to improve the composition but in an amount to minimize foaming of the composition upon physical mixing or dilution into water.

Generally the amount of any nonionic surfactant is from 0.1 to 1% of the composition, preferably from 0.1 to 0.5% by weight of the composition.

A general description of surfactants that might be used include nonionic surfactants such as $C_8$ to $C_{18}$ alcohol alkoxylates, both linear and branched chain ethoxylates with 2 to 22 (preferably 2 to 10) ethylene oxide (EO) units; alkyl phenol ethoxylates, mono- and di-nonyl and octyl phenol with 2 to 150 (preferably 2 to 40) EO units, fatty amine alkoxylates, e.g., tallow, oleyl, stearyl and cocoamine alkoxylates with 2 to 50 EO (preferably 2 to 20) units; alkanolamides; triglyceride alkoxylates, such as castor, rapeseed, soybean and colza oil ethoxylates with 5 to 54 (preferably 5 to 20) EO units; sorbitan ester ethoxylates with 20 to 30 EO units, ethylene oxide/propylene oxide copolymers including alkoxylated rapeseed oil with ethylene oxide and propylene oxide chains; alkyl polyglycosides; fatty acid ethoxylates; fatty acid polyethylene glycols; fatty alcohol ethoxylates; di- and tristyrylphenol ethoxylates; glycerol esters; and polyol ethoxylate esters.

Polysorbates are a class of emulsifiers that can be used in the compositions described herein. Polysorbates are oily liquids derived from PEG-ylated sorbitan (a derivative of sorbitol) esterified with fatty acids. Surfactants that are esters of plain (non-PEG-ylated) sorbitan with fatty acids are usually referred to by the name Span.

Examples include, but are not limited to:

Polysorbate 20 (Tween 20 or polyoxyethylene (20) sorbitan monolaurate)

Polysorbate 40 (Tween 40 or polyoxyethylene (20) sorbitan monopalmitate)

Polysorbate 60 (Tween 60 or polyoxyethylene (20) sorbitan monostearate)

Polysorbate 80 (Tween 80 or polyoxyethylene (20) sorbitan monooleate)

The number 20 following the polyoxyethylene part refers to the total number of oxyethylene —$(CH_2CH_2O)$— groups found in the molecule. The number following the polysorbate part is related to the type of fatty acid associated with the polyoxyethylene sorbitan part of the molecule. Monolaurate is indicated by 20, monopalmitate is indicated by 40, monostearate by 60 and monooleate by 80. The same numbering is followed in their Span equivalents (Span 20, Span 40, Span 60 and Span 80).

Representative anionic surfactants include sulfates, fatty alcohol ether sulfates, fatty acid sulfates; sulfonates, alkylbenzenesulfonates, alkyl naphthalene sulfonates, alkylaryl sulfonates, olefin sulfonates, alkylphenol ethoxylate sulfates; phosphates, such as phosphates of fatty alcohol ethoxylate, phosphates of alkylphenol ethoxylate having 4 to 12 EO units; alkyl sulfosuccinates; carboxylates, alkylphenol ethoxylate carboxylates.

The compositions in accordance with the present invention may be formulated in any suitable manner appropriate to the ingredients involved. Representative formulations are described below.

II. Formulations Including the Active Agents Described Herein

As described in more detail below, the formulations including the active agents described herein can be in various liquid or solid forms, either for application to a human or other animal, or to an article or locus. The various formulation types are described in detail below.

Formulations for Application to Animals or Humans

The composition can be formulated as a lotion composition for administration to the skin of user. Such compositions may also contain, as inert ingredients, purified water, coconut oil, glycerin, geranium oil, citric acid, lecithin, sodium bicarbonate and vanilla.

The compositions can also be formulated as spray compositions, for example, for administration to the skin or fur of pets. Such compositions may contain 2% by weight of soy methyl ester, purified water, coconut oil, glycerin, geranium oil, castor oil, lecithin and vanilla.

In one embodiment of the invention, the composition is formulated as a spray composition for administration to the skin of a user. Such composition may contain from 0.1 to 15% by weight of the active agents, in a carrier base including, as inert ingredients, purified water, coconut oil, glycerin, geranium oil, citric acid, lecithin, sodium bicarbonate and vanilla.

Other compositions of the invention may be formulated as sunblock compositions, containing, in addition to soy methyl ester, zinc oxide, titanium dioxide, and/or small amounts of other sunscreen agents, as well as ingredients such as coconut oil, purified water, glycerin, geranium oil, citric acid, lecithin, sodium bicarbonate, and vanilla.

Useful formulations for applying the compositions to an animal or a human, to combat pests such as mosquitoes, ticks, and the like, are advantageously formulated as an emulsified base to which are added carrier, adjuvant and other ingredients of the composition.

Formulations for Application to a Locus

In addition to compositions of the invention that are formulated for application to body surfaces of users, compositions may be formulated for application or administration to any locus in which it is desired to repel pests against which the compositions of the invention are repellently effective. Such loci may contain or include apparel, furniture, personal accessories, plastic products, cloth products, camping equipment, automotive and vehicular interiors, and the like. For indoor or outdoor usage, the compositions of the invention may be formulated for broadcasting by misting systems or other distribution equipment.

Formulations for Spray and Aerosol Applications

Aerosol formulations typically include the active agents and a suitable propellant (for example, n-butane). Alternatively, the active agents can be dissolved or dispersed in a suitable medium, such as water or a water-miscible liquid, such as n-propanol, to provide compositions for use in non-pressurized, hand-actuated spray pumps.

Ideally, the aerosol formulations provide a quick kill and rapid knock-down to flying insects. While not wishing to be bound to a particular theory, it is believed that the presence of fatty acids provides both a rapid knock-down and quick kill to flying insects such as bees, wasps, hornets, mosquitoes, flies, and the like.

In any of these forms, the formulations can include a propellant, so that they can be aerosolized. Such aerosolized compositions can be used in fumigation applications, such as ship/air cargo or food containment areas. The compositions can also be used as a pesticide treatment prior to transporting items. In one embodiment, the compositions are converted to aerosol compositions by adding nitrogen to the formula, and keeping the contents in a pressurized container, such as a metal can. Nitrogen is an inert additive, and not a green-house gas, and can be preferred over other propellants, such as low molecular weight hydrocarbons. When present, the nitrogen is present in an amount of up to 10 percent, though is typically in the range of about 0.5% by weight of the composition.

The aerosol compositions can also include a propellant other than nitrogen, such as n-propane, n-butane, iso-pentane, iso-butane, n-pentane or hydrofluorocarbons.

Dispersible Concentrates

Dispersible Concentrates (DC) may be prepared by dissolving the active compounds in water or an organic solvent, such as silicon oil, vegetable oil, or soy methyl ester. These solutions may contain, in addition to sodium lauryl sulfate, an additional surface active agent (for example to improve water dilution or prevent crystallization in a spray tank).

Solid Compositions

While the compositions described herein are mainly exemplified by liquid formulations, they can also exist as solids, where the sodium lauryl sulfate is in the form of a solid salt rather than being present in solution, and the fatty acids, when present (which typically are low melting solids) are either in solid form, or are adsorbed or absorbed into a solid carrier material. The soy methyl ester and/or undecanone, when present, can also be adsorbed or absorbed into a solid carrier material.

Solid homogenous or heterogenous compositions containing one or more active compounds described herein, for example, dusts (also known as dusting powders, dustable powders, and soluble powders), with a content of the active compounds described herein ranging up to 80%), wettable powders or granules, (including water-soluble and water-dispersible granules), particularly those obtained by extrusion, compacting, impregnation of a granular carrier, or granulation starting from a powder (the content of the active compounds described herein, in these wettable powders or granules, being between about 0.5 and about 80%), baits, pellets, briquettes or capsules, may be used.

The formulation type chosen in any instance will depend upon the particular purpose envisaged and the physical, chemical and biological properties of the active compounds described herein.

Dustable powders (DP) may be prepared by mixing the active components described herein with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing the active components described herein with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) (or powder for spraying) may be prepared by mixing the active compounds described herein with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG). Each of these may be dissolved or suspended in water to give any desired concentration and the resulting solution or suspension can be employed very advantageously in particular for application to plant foliage.

Wettable powers are usually prepared so that they contain from about 10 to about 80% by weight of active ingredients, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like.

Granules (GR) may be formed either by granulating the active compounds described herein and one or more powdered solid diluents or carriers, or from pre-formed blank granules by absorbing the active compounds described herein (or a solution thereof, in a suitable agent) in a porous granular material (such as pumice, attapulgite clays, fuller's earth, kieselguhr, diatomaceous earths or ground corn cobs) or by adsorbing the active compounds described herein (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

"Water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

In some embodiments, the solid compositions can include lubricants. Representative lubricants include precipitated silica and fumed alumina. Fumed alumina is produced by the hydrolysis of aluminum trichloride in a hydrogen-oxygen flame. The combustions process creates aluminum oxide molecules which condense to form primary particles which sinter together to form aggregates. These aggregates have a chain-like structure and an average diameter of 0.1 and 0.2 microns. Fumed alumina, like precipitated silica, has small particle size in the submicron range (for primary particle size of 20 nm and aggregate size of 150 nm) down to nanometer particle size with B.E.T. surface area of 55 m$^2$/g. It also provides rheology control and lubrication for the suspension concentrate.

Clays may also be optionally used in the present composition. Such clays include kaolinite, dickite, and nacrite, with the general formula of $Al_2Si_2O_5(OH)_4$; pyrophylite, talc, vermiculite, sauconite, saponte, nontronite, and montmorillonite with the general chemical formula $(Ca,Na,H)(Al,Mg,Fe,Zn)_2(Si,Al)_4O_{10}(OH)_2 \cdot xH_2O$; attapulgite with the general chemical formula $Mg_5Si_8O_{20}(HO)_2(OH_2)_4 4H_2O$; and illite with the general formula $(K,H)Al_2(Si,Al)_4O_{10}(OH)_2 \cdot xH_2O$.

The rates and concentrations of the formulated compositions may vary according to the method of application or the nature of the compositions or use thereof.

III. Types of Pests that can be Treated

The compositions can be used to combat and control infestations of a variety of pests.

Pest species include arthropod pests, agricultural, horticulture, and garden pests, rodent pests and reptile and amphibian pests. Arthropod pests include aphids, ants, bed bugs, bees (e.g. carpenter bees), beetles, centipedes, caterpillars, chiggers, cockroaches, crickets, cutworms, earwigs, fleas, flies (e.g., house flies, black flies, white flies, deer flies, fruit flies, horse flies, horn flies, midges, stable flies, etc.), fire ants, gnats, grasshoppers, hookworms, Japanese beetles, June bugs, lice, locust, mealworms, mealybugs, millipedes, mites, mosquitoes, moths, pillbugs, scorpions, silverfish, spiders, stinkbugs, termites, thrips, ticks, and wasps. Agriculture, horticulture and garden pests include aphids, beetles, caterpillars, cutworms, maggots, mealybugs, mites (e.g. spider mites), moths, stinkbugs, thrips, and white flies. Rodent pests include chipmunks, mice, rats, squirrels and voles. Reptile and amphibian pests include lizards, snakes, and frogs.

Specific pests that were evaluated included flying insects, including flies and wasps, lice, mites, spiders, carpenter bees, chiggers, ticks, fleas, ants, including fire ants, aphids, beetles (potato and bean), flea beetles, Japanese beetles, silver fish, cockroaches, fleahoppers, thrips, squash bugs, slugs, leaf hoppers, harlequin bugs and milk weed bugs. Representative insects that can be repelled using the compositions described herein include caterpillars, maggots, moths, and grasshoppers. Rodents and deer were also repelled with some formulations.

Based on the data on these specific pests, it is believed that the compositions will be effective against a broad spectrum of pests, such as *Lepidoptera, Diptera, Hemiptera, Thysanoptera, Orthoptera, Dictyoptera, Coleoptera, Siphonaptera, Hymenoptera* and *Isoptera* and also other invertebrate pests, for example, acarine, nematode and mollusc pests. Insects, acarines, nematodes and molluscs are hereinafter collectively referred to as pests. The pests which may be combated and controlled include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis*, (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neoterines* spp.), the *Rhinotermitidae* (for example *Coptotermes formosanus, Reticulitermes flavipes, R. speratu, R. virginicus, R. hesperus,* and *R. santonensis*) and the *Termitidae* (for example *Globitermes sulphureus*), *Solenopsis geminata* (fire ant), *Monomoriumn pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), and *Trichostrongylus* spp. (gastro intestinal nematodes).

IV. Pesticidal Methods of Treatment

The compositions described herein can be used to treat pest infestations in crop loci, storage areas, property, and the like, and to treat animals and humans exposed to, or likely to be exposed to, one or more pests. Individual methods of treatment are described in more detail below. In some embodiments, the compositions are used in agricultural applications, and can be non-phytotoxic or nearly so. In one particularly preferred embodiment, the compositions are used as a fire ant drench. Where pests contribute allergens, the compositions can optionally include an enzyme to assist with controlling allergens.

Treatment of Cargo/Food Containers/Storage Areas

The compositions can be applied to cargo holds, food containers, and storage areas, for example, by fumigation, to control pests. Some of the formulas described herein are capable of being organically certified, and, when the compositions are intended for application to food containers, it is preferable that such compositions are applied.

In these embodiments, the compositions can help prevent the spread of insects, arthropods, and other pests from one location to another, whether from one country to another, in the case of international shipments, or from one geographic area to another within the same country, in the case of domestic shipments.

Treatment of Specific Loci, Including Crop Loci

The compositions can be used to protect field, forage, plantation, glasshouse, orchard or vineyard crops, of ornamentals, or of plantation or forest trees, for example: cereals (such as wheat or rice), cotton, vegetables (such as peppers), field crops (such as sugar beets, soybeans or oil seed rape), grassland or forage crops (such as maize or sorghum), orchards or groves (such as of stone or pit fruit or citrus), ornamental plants, flowers or vegetables or shrubs under glass or in gardens or parks, or forest trees (both deciduous and evergreen) in forests, plantations or nurseries.

The compositions can also be used to protect timber (standing, felled, converted, stored or structural) from attack, for example, by sawflies or beetles or termites.

The compositions can be used to protect stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack. In these embodiments, the naturally-occurring and safe nature of the active agents is particularly relevant.

The compositions can be applied to grasses, shrubs, vegetable gardens, and fruit trees, in some embodiments, without phytotoxicity or with minimal phytotoxicity. As used herein, minimal phytotoxicity means that the leaves may experience browning by appearance, but no killing or degradation to the plant, nor prevention of plant growth.

The amounts in which the compositions are applied can be varied within a substantial range. They are generally on the order of magnitude which is conventionally chosen for the application of "attract-and-kill formulations."

Suitable means of applying the compositions to growing crops include as foliar sprays (for example as an in-furrow spray), fogs or foams.

Suitable means of applying the compositions to soil or roots include liquid drenches, smokes or foams. When a pest is soil-borne, the composition is distributed evenly over the area to be treated (i.e, for example broadcast or band treatment) in any convenient manner and is applied at rates from about 10 g/ha to about 400 g/ha, preferably from about 50 g/ha to about 200 g/ha. Application may be made, if desired, to the field or crop-growing area generally or in close proximity to the seed or plant to be protected from attack. The compositions can be applied before planting, at planting, or after planting but ideally before sprouting has taken place, or after sprouting. When used as a drench, the formulations can be particularly effective against all ant species, including as fire ants, carpenter ants, red imported fire ants, Argentine ants, odorous house ants, pavement ants, and moisture ants.

Suitable means of applying the compositions to crop seeds include application as seed dressings, e.g. by liquid slurries.

The compositions described herein can be applied to plants or areas under cultivation in the form of droplets, drop-like areas or thin defined layers by using conventional devices as they are known to those skilled in the art. Fruit-bearing trees or of vines can advantageously be treated by applying the compositions using dosing dispensers, pipettes or syringes, brushing devises, or surface nozzles to distribute the compositions over a substantial area.

Suitable means of applying the compositions to the environment in general or to specific locations where pests may lurk, including stored products, timber, household goods, or domestic or industrial premises, include sprays, fogs, dusts, smokes, lacquers, or baits.

In this embodiment, the compositions are generally applied to the locus in which the pest infestation is to be controlled at an effective rate in the range of about 2 g to about 1 kg of the active compounds per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. Preferably an effective rate range of the active compound is from about 10 g/ha to about 400 g/ha, more preferably from about 50 g/ha to about 200 g/ha.

Animal Treatment

The compositions can be used to control arthropods or helminths which are injurious to, or spread or act as vectors of diseases domestic animals, for example those hereinbefore mentioned, and more especially in the control of ticks, mites, lice, fleas, midges, or biting, nuisance or myiasis flies.

Suitable means of applying the compositions to animals infested by or exposed to infestation by arthropods or helminths, include topical application, such as by using pour-on formulations, sprays, baths, dips, showers, jets, dusts, greases, shampoos, creams, wax smears or livestock self-treatment systems. The frequency of treatment of the animal, preferably the domestic animal to be treated by the compositions, is generally from about once per week to about once per year, preferably from about once every two weeks to once every three months.

Addition of Enzyme to Aid in Allergen Control

In some embodiments, the compositions can include an enzyme to assist with allergen control, for example, allergens contributed by pests.

Although allergens are not specifically considered a pest, examples of allergens include pollen, pet dander, mite and roach feces, and the like. The and other allergens produced by pests (i.e., "pest-produced allergens") can be controlled by administering the compositions described herein with an enzyme that degrades the allergens.

One representative enzyme is Subtilisin [CAS 9014-01-1], although others include the enzymes in Kleen Kill® and Bactozyme®. Proteases are a specifically-preferred class of enzymes for metabolizing pest-produced allergens. The term "protease" as used herein collectively denotes enzymes having properties for decomposing proteins and peptides. The enzymes available in the invention may be any one of acidic, neutral and basic proteases known in the art, per se. For example, they may be serine proteases such as trypsin, cysteine proteases such as papain, calpain and cathepsin B and cathepsin L, aspartic acid proteases such as pepsin, renin and cathepsin D, and proteases such as metalloproteases. The types and concentrations of enzymes can be appropriately selected by those of skill in the art, with the knowledge of the particular type of allergen to be degraded.

In one embodiment, when the compositions include the enzymes, they further include 2-undecanone or rue oil. This combination of active agents (i.e., enzyme and undecanone or rue oil) additive increases the toxicity to hard bodied arthropods.

The advantages and features of the invention are further illustrated with reference to the following examples, which are not to be construed as in any way limiting the scope of the invention but rather as illustrative of embodiments of the invention in specific applications thereof.

EXAMPLE 1

Representative Compositions

Specific Formulations:
Note: Emulsifiers may vary and individual formulant concentrations may vary to yield a finished product with the desired consistency.

Formulation V: Sodium Lauryl Sulfate in Soybean Oil+Fatty Acids Oil in Water Emulsion

| | |
|---|---|
| Water | 75.0% |
| Sodium Lauryl Sulfate | 5.8% |
| Vegetable Oil (Soybean Oil and coconut Oil used) | 8.0% |
| Coconut Oil Fatty Acids (C810 by P&G) | 8.0% |
| Soy Lecithin or polysorbate 20 | 2% |
| Sodium Bicarbonate | 1.0% |
| Benzoic Acid, Sodium Salt | 0.2% |
| Total: | 100% |

Formulation V1: Sodium Lauryl Sulfate in Soybean Oil+Water (No FA)

| | |
|---|---|
| Water | 64.2% |
| Sodium Lauryl Sulfate | 5.8% |
| Soybean Oil | 30% |
| Total: | 100% |

Formulation V2: Sodium Lauryl Sulfate in Coconut Oil+Water (No FA)

| | |
|---|---|
| Water | 64.2% |
| Sodium Lauryl Sulfate | 5.8% |
| Coconut Oil Triglyceride | 30% |
| Total: | 100% |

Formulation W: Sodium Lauryl Sulfate in Silicone Oil+Fatty Acids Oil in Water Emulsion

| | |
|---|---|
| Water | 75% |
| Sodium Lauryl Sulfate | 5.8% |
| Coconut Oil Fatty Acids (C810 by Proctor & Gamble) | 8.0% |
| Cyclomethicone silicone oil (DC 345 of Dow Corning) | 8.0% |
| Polysorbate 20 | 2.0% |
| Sodium Bicarbonate | 1.0% |
| Benzoic Acid, Sodium Salt | 0.2% |
| Total: | 100% |

Formulation W1: Sodium Lauryl Sulfate in Silicone Oil+Water (No FA)

| | |
|---|---|
| Water | 74.2% |
| Sodium Lauryl Sulfate | 5.8% |
| Cyclomethicone (DC 345 of Dow Corning) | 20% |
| Total: | 100% |

Formulation X: Sodium Lauryl Sulfate in SME+Fatty Acids Oil in Water Emulsion

| | |
|---|---|
| Water | 85.2% |
| Sodium Lauryl Sulfate | 5.8% |
| Soybean Methyl Ester (SME) | 6% |
| Coconut Oil Fatty Acids (C810 by Proctor & Gamble) | 3% |
| Total: | 100% |

Formulation X1: Sodium Lauryl Sulfate in SME Low Percentage+Water (No FA)

| | |
|---|---|
| Water | 88.2% |
| Sodium Lauryl Sulfate | 5.8% |
| Soybean Methyl Ester (SME) | 6% |
| Total: | 100% |

Formulation X2: Sodium Lauryl Sulfate in SME High Percentage+Water (No FA)

| | |
|---|---|
| Water | 64.2% |
| Sodium Lauryl Sulfate | 5.8% |
| Soybean Methyl Ester (SME) | 30% |
| Total: | 100% |

Formulation Y: Sodium Lauryl Sulfate with Undecanone Least-Phytotoxic Formulation

| | |
|---|---|
| Water | 67% |
| Sodium Lauryl Sulfate | 6% |
| Coconut Oil Triglyceride (Capric/Caprylic Triglyceride) | 4% |
| Coconut Fatty Acid C810 (Proctor & Gamble) | 2% |
| Soybean Oil | 4% |
| Soy Methyl Ester | 4% |
| Undecanone | 4% |
| Silicone Oil (DC 345) | 4% |
| Polysorbate 20 | 2% |
| Sodium Bicarbonate | 0.5% |
| Benzoic Acid | 0.4% |
| Fragrance (Lavender) | 1% |
| Fragrance (Lemongrass Oil) | 0.6% |
| Fragrance (Menthol or Peppermint Oil) | 0.5% |
| Total: | 100% |

Formulation Z: Shampoo Insecticide with Sodium Lauryl Sulfate+Fatty Acids

| | |
|---|---|
| Water | 40% |
| Sodium Lauryl Sulfate | 8% |
| Cocamide DEA | 3% |
| Cocamidopropyl betaine | 4% |

| | |
|---|---|
| Olefin Sulfonate | 2% |
| Coconut Oil Triglyceride (Capric/Caprylic Triglyceride) | 6% |
| Coconut Fatty Acid C810 (Proctor & Gamble) | 6% |
| Soybean Oil | 8% |
| Soy Methyl Ester | 8% |
| Silicone Oil (DC 345) or Polysorbate 20 | 8% |
| Hydrogenated Castor Oil or Soy Lecithin | 2% |
| Lauric Acid | 1% |
| Citric Acid | 1% |
| Sodium Bicarbonate | 0.5% |
| Benzoic Acid | 0.4% |
| Fragrance (Lavender) | 1% |
| Fragrance (Lemongrass Oil or Citral) | 0.6% |
| Fragrance (Menthol or Peppermint Oil) | 0.5% |
| Total: | 100% |

EXAMPLE 2

Evaluation of the Knock Down and Time to Mortality

The time various compositions take to both knock down (KD) and kill (TM) various pests was determined. As a control, results were compared using sodium lauryl sulfate by itself, and with the various fatty acids.

Insects that were evaluated included flying insects, including flies and wasps, ticks, fleas, ants, including fire ants, aphids, Japanese beetles, silver fish, and cockroaches.

The tests were conducted for a maximum observation time of 30 minutes, after which time, the test, and all observations, was stopped.

The individual testing protocols for each type of pest are described below:

Flying Insects

Protocol: Each formula was put in a 16 oz bottle with trigger sprayer and sprayed on a broad area where the insect was flying or resting. The average weight per area of spray was calculated. Insects specifically tested by this method included common house flies, mosquitoes (Asian Tiger species), beetles (Japanese beetle), and moths (species undetermined) while the duration in seconds was observed for Knock Down (KD). Duration from contact of product to mortality (MT) was observed in seconds or minutes over a 30 minute observation. Observation was discontinued at 30 minutes. See results in table above. Application rate was approximately 0.01 oz per square inch or otherwise specified in the table above.

Ticks

Protocol: Ticks (Lone Star species) were individually sprayed while traveling on the ground. The average amount of material per area was calculated. The amount of material to kill the Tick was determined.

Fleas

Protocol: A light colored cotton towel was dragged across the sand and let rest in an area where sand fleas were prevalent. The area on the towel where the sand fleas landed was sprayed with the material using a trigger sprayer. The amount of material to kill the fleas was determined.

Ants

Protocol: Ants (undetermined species) were individually sprayed while traveling on an indoor kitchen countertop. The average amount of material per area was calculated. The amount of material to kill the Ant was determined.

Fire Ants

Protocol: Fire ants (Red Imported species) were directly sprayed while traveling on the ground. The average amount of material per area was calculated. The amount of material to kill the Fire Ant was determined.

Ag Insects (Aphids)

Protocol: Areas of vegetation containing aphids were sprayed with material using a trigger sprayer. The average amount of material per area was calculated. The time to mortality was observed.

Japanese Beetles

Protocol: Areas of Crepe Myrtle trees were sprayed containing Japanese Beetles with material using a trigger sprayer. The average amount of material per area was calculated. The time to mortality was observed.

Spiders

Protocol: Spiders (Wolf species) were directly sprayed while traveling on the ground. The average amount of material per area was calculated. The amount of material to kill the Spider was determined.

Termites

Protocol: Termites (undetermined species) on the underside of a wood pile were sprayed with a trigger sprayer of material. The average amount of material per area was calculated. The amount of material to kill the Termites was determined.

Wasps

Protocol: The area where a Wasp was in flight or resting was sprayed using a trigger sprayer. The minimum amount to kill the wasp in flight or while landed was determined as indicated in the table.

Silver Fish

Protocol: Silver Fish (undetermined species) were individually sprayed while traveling on an outdoor area of concrete. The average amount of material per area was calculated. The amount of material to kill the Silver Fish was determined.

Cockroaches

Beer was poured on a concrete floor in a garage to attract cockroaches. The cockroach was individually sprayed while feeding on the beer. The average amount of material used was calculated.

Note: Mite and lice testing has not been conducted. However, based on the results of this example, the compositions and methods would apply to mites and lice, as well as other insects and arthropods not directly listed.

Table 1 describes the Efficacy results and resulting claims comparing SLS to SLS and Fatty Acids of Capric and Caprylic (nearly 50/50 but encompass any mixture). Table 2 compares Knock Down and cidal activity of SLS formulations without FAs of capric and caprylic.

TABLE 1

EFFICACY RESULTS - comparison of SLS + FA (capric/caprylic) formulas to SLS

| | Formula U | Formula V | Formula W | Formula X | Formula Y | Formula Z |
|---|---|---|---|---|---|---|
| Formulation Description | Sodium Lauryl Sulfate in water dilution using SLS CONTROL | Sodium Lauryl Sulfate in Soybean Oil + Fatty Acids oil in water emulsion | Sodium Lauryl Sulfate in Silicon oil + Fatty Acids oil in water emulsion | Sodium Lauryl Sulfate in SME + Fatty Acids oil in water emulsion | Sodium Lauryl Sulfate with undecanone (least-phytotoxic formulation) low amount of FA | shampoo Insecticide with Sodium Lauryl Sulfate + Fatty Acids |
| Specific Formulation | Diluted 1 part Chemistry Store material (29% solution) with additional 4 parts water for 5.8% total SLS solution | SLS 5.8% See other formulants in Specific Formulation section below | SLS 5.8% See other formulants in Specific Formulation section below | SLS 5.8% See other formulants in Specific Formulation section below | SLS 5.8% See other formulants in Specific Formulation section below | SLS 8% See other formulants in Specific Formulation section below |
| Claims | Range of 0.1 to 10 percent SLS for KD and MT enhancement to following formulas. | SLS + vegetable Oil (soybean oil or Coconut Oil) + Fatty Acids is highly insecticidal with excellent KD and MT | SLS + Silicone oil (DC 345) + Fatty Acids is highly insecticidal with excellent KD and MT | SLS + modified fatty acid (Soy Methyl Ester) + Fatty Acids is highly repellent and insecticidal with excellent KD and MT | SLS + SME + undecanone is highly repellent and insecticidal with excellent KD and MT; particularly effective at killing wasps quickly | SLS + Fatty Acids is insecticidal with excellent KD and MT |
| Knock Down (KD) and Mortality (MT) Efficacy Results | Small Fly KD < 1 sec Dropped to ground and started walking after a couple minutes. Would not fly during observed time. MT > 30 min | Small Fly KD = immed MT < 30 sec | Small Fly KD = immed MT < 30 sec | Small Fly KD = immed MT < 10 sec | Small Fly KD = immed MT < 10 sec | Small Fly Landed MT < 10 sec |
| | Large Fly KD < 1 sec MT > 30 min | Large Fly KD < 5 sec MT = 5 min | Large Fly KD < 5 sec MT = 5 min | Large Fly KD < 1 sec MT < 1 min | Large Fly KD < 1 sec MT < 1 min | Large Fly Landed MT < 20 sec |
| | Aphid MT > 10 sec | Aphid MT = immed | Aphid MT = immed | Aphid MT = immed | Aphid MT = immed | Aphid MT = immed |
| | Mosquito KD < 1 sec MT = 5 min | Mosquito KD = immed MT = immed | Mosquito KD = immed MT = immed | Mosquito KD = immed MT = immed | Mosquito KD = immed MT = immed | Mosquito KD = immed MT = immed |
| | Moth MT > 30 min | Not tested | Not tested | Moth (1 ml) KD < 1 sec MT = 2 min | Moth (1 ml) KD < 1 sec MT = 2 min | Not tested |
| | Fleas KD = 10 seconds MT = 1 minute | Fleas KD = immed MT = immed | Fleas KD = immed MT = immed | Fleas KD = immed MT = immed | Fleas KD = immed MT = immed | Fleas KD = immed MT = immed |
| | Ticks (4 ml) MT > 30 min | Tick (2 ml) MT = 4 min (repellent on human skin) | Not tested | Tick (1 ml) MT < 60 sec (repellent on human skin) | Tick (1 ml) MT < 60 sec (repellent on human skin) | Tick (1 ml) MT < 30 sec (repellent on animal skin) |
| | Roaches (8 ml) Nymph | Adult Roach (4 ml) | Adult Roach (4 ml) | Adult Roach | Adult Roach (4 ml) | Adult Roach (4 ml) |

TABLE 1-continued

EFFICACY RESULTS - comparison of SLS + FA (capric/caprylic) formulas to SLS

|  | Formula U | Formula V | Formula W | Formula X | Formula Y | Formula Z |
|---|---|---|---|---|---|---|
|  | MT > 30 min | MT < 30 sec Nymph Roach (2 ml) MT < 5 sec | MT < 30 sec Nymph Roach (2 ml) MT < 5 sec | (4 ml) MT < 30 sec Nymph Roach (2 ml) MT < 5 sec | MT < 30 sec Nymph Roach (2 ml) MT < 5 sec | MT < 30 sec Nymph Roach (2 ml) MT < 5 sec |
|  | Ants (2 ml) MT = immed FIRE ANTS Application rate = 4 ml MT = No effect | Ants (1 ml) MT = immed FIRE ANTS Applicaton rate = 2 ml MT = 30 sec | Ants (1 ml) MT = immed FIRE ANTS Application rate = 2 ml MT = 30 sec | Ants (1 ml) MT = immed FIRE ANTS Application Rate = 1 ml MT = 20 sec | Ants (1 ml) MT = immed FIRE ANTS Application Rate = 1 ml MT = 20 sec | Not tested Not tested |
|  | Spider (8 ml) MT = no effect | Spider (4 ml) MT < 2 min | Not tested | Spider (4 ml) MT < 1 min | Spider (4 ml) MT < 30 sec | Spider(2 ml) MT = 10 sec |
|  | Jap Beetle (8 ml) MT = no effect | Jap Beetle (4 ml) MT < 5 sec | Jap Beetle (4 ml) MT < 5 sec | Jap Beetle (4 ml) MT < 5 sec | Jap Beetle (4 ml) MT < 5 sec | Not tested |
|  | Termite (1 ml) MT = 20 sec Wasps (8 ml) KD < 5 sec MT = no effect | Termite (1 ml) MT < 20 sec Wasp (4 ml) KD < 5 sec MT = 30 sec | Termite (1 ml) MT < 20 sec Not tested | Termite (1 ml) MT < 20 sec Wasp (4 ml) KD < 1 sec MT = 20 sec | Termite (1 ml) MT < 20 sec Wasp (2 ml) KD < 1 sec MT = 20 sec | Termite (1 ml) MT < 20 sec Not tested |
|  | Silver Fish (2 ml) MT = no effect | Silver Fish (2 ml) MT < 3 sec | Not tested | Silver Fish (2 ml) MT < 3 sec | Not tested | Not tested |
| Dilution Comparison | FIRE ANTS Application rate = 4 ml observed for 10 minutes 1% SLS MT = no effect 5% SLS MT = no effect 10% SLS MT = no effect (note, it took 20 ml of aqueous 10% SLS mixture to kill the fire ant.) | FIRE ANTS Application rate = 2 ml MT = 30 sec | FIRE ANTS Application rate = 2 ml MT = 30 sec | FIRE ANTS Application Rate = 1 ml MT = 20 sec | FIRE ANTS Application Rate = 1 ml MT = 20 sec | Not Tested |

Results

The results outlined in Table 1 are summarized below.

Effectiveness Against Small Flies

With respect to small flies, the data in Table 1 show that sodium lauryl sulfate, by itself, was able to immediately knock down flies, but not kill them. When fatty acids were added, alone or in combination with vegetable oil, silicon oil, or soy methyl ester, the time to kill went from greater than 30 minutes, to less than 30 seconds. Thus, the combination of sodium lauryl sulfate and fatty acids provided instant knockdown and almost instant kill. The results did not vary significantly between using vegetable oil, silicon oil, or soy methyl ester. With very low amounts of fatty acids, and the use of undecanone, the composition also provided an almost instant kill Effectiveness Against Large Flies With respect to large flies, the data in Table 1 show that sodium lauryl sulfate, by itself, was able to immediately knock down flies, but not kill them. When fatty acids were added, alone or in combination with vegetable oil, silicon oil, or soy methyl ester, the time to kill went from greater than 30 minutes, to five minutes when vegetable oil or silicon oil were added, to less than one minute when soy methyl ester was used. Thus, soy methyl ester functioned better than vegetable oil or silicon oil in this regard, providing both instant knockdown and almost instant kill With very low amounts of fatty acids, and the use of undecanone, the composition also provided an almost instant kill (i.e., less than one minute).

Effectiveness Against Aphids

With respect to aphids, the data in Table 1 show that sodium lauryl sulfate, by itself, was able to almost immediately kill then (i.e., greater than 10 seconds). When all of the other formulations were tested, they provided an instant kill Effectiveness Against Mosquitoes With respect to mosquitoes, the data in Table 1 show that sodium lauryl sulfate, by itself, was able to immediately knock down mosquitoes, but to kill them, it took around five minutes. When all of the other formulations were tested, they provided an instant kill. Thus, the addition of fatty acids, regardless of the other ingredients, provided an instant kill.

Effectiveness Against Moths

With respect to moths, the data in Table 1 show that sodium lauryl sulfate, by itself, was unable to kill the moths, even at thirty minutes past exposure. Two other formulations were tested, namely, those with either soy methyl ester, or undecanone. Both showed the ability to kill moths within around two minutes of exposure.

Effectiveness Against Fleas

With respect to fleas, the data in Table 1 show that sodium lauryl sulfate, by itself, showed the ability knock down fleas in around ten seconds, and take around one minute to kill them. In contrast, when all of the other formulations were tested, they provided an instant knockdown and instant kill.

Effectiveness Against Ticks

With respect to ticks, the data in Table 1 show that sodium lauryl sulfate, by itself, was unable to kill them, even after thirty minutes of exposure. When fatty acids and soybean oil were added, the composition acted as a repellent, and also killed the ticks in around four minutes. All of the other formulations were tested, except for the formulation including silicon oil. All provided both insect repellent properties, and killed the ticks within one minute of exposure.

Effectiveness Against Roaches

With respect to roaches, the data in Table 1 show that sodium lauryl sulfate, by itself, was unable to kill nymph, even after thirty minutes of exposure. All of the other formulations were tested, and killed the adult roach in less than thirty seconds, and the nymph in less than five seconds.

Effectiveness Against Ants

With respect to ants, the data in Table 1 show that all formulations tested, including sodium lauryl sulfate by itself, and all of the other formulations except the shampoo including fatty acids, immediately killed the ants.

With respect to fire ants, sodium lauryl sulfate by itself did not have the ability to kill the fire ants. However, the formulations that included the fatty acids and either silicon oil or soybean oil killed the fire ants within thirty seconds. The formulations that included the fatty acids and soy methyl ester, and that included a low amount of fatty acids, in combination with undecanone, both killed the fire ants within twenty seconds.

A dilution study was done using just sodium lauryl sulfate and water. It took around 20 ml of an aqueous 10% sodium lauryl sulfate solution to kill the fire ants. No other dilution (1% or 5%) had any effect.

Effectiveness Against Spiders

With respect to spiders, the data in Table 1 show that sodium lauryl sulfate, by itself, was unable to kill them, even after thirty minutes of exposure. When fatty acids and soybean oil were added, the composition killed the spiders in less than two minutes. When fatty acids and soy methyl ester were added, the spiders were killed in less than one minute. When undecanone was added, the spiders were killed in less than thirty seconds. The shampoo formulation including sodium lauryl sulfate and the fatty acids killed the spiders in around ten seconds.

Effectiveness Against Japanese Beetles

With respect to Japanese beetles, the data in Table 1 show that sodium lauryl sulfate, by itself, was unable to kill them, even after thirty minutes of exposure. All other formulations tested (all but the shampoo formulation were tested) killed the Japanese beetles in less than five seconds.

Effectiveness Against Termites

With respect to termites, the data in Table 1 show that sodium lauryl sulfate, by itself, was able to kill termites in around 20 seconds. All of the other formulations were tested, and each killed the termites in under twenty seconds.

Effectiveness Against Wasps

With respect to wasps, the data in Table 1 show that sodium lauryl sulfate, by itself, was able to almost instantaneously knock them down (i.e., knockdown in less than five seconds), but unable to kill them, even after thirty minutes of exposure. When formulations including fatty acids and silicon oil, soy methyl ester, or undecanone were tested, the compositions killed the wasps in around thirty, twenty, and twenty seconds, respectively.

Effectiveness Against Silver Fish

With respect to silver fish, the data in Table 1 show that sodium lauryl sulfate, by itself, was unable to kill them, even after thirty minutes of exposure. When formulations including fatty acids and silicon oil or soy methyl ester were tested, the compositions each killed the silver fish in less than three seconds.

To verify that the results were due to the combination of fatty acids and sodium lauryl sulfate, and not solely due to the presence of silicon oil, soybean oil, or soy methyl ester, additional formulations were tested. These formulations included:

Formula V1—Sodium lauryl sulfate in a soybean oil in water emulsion

Formula V Formula VI—Sodium lauryl sulfate in a soybean oil in water emulsion

Formula W1—Sodium lauryl sulfate in a silicon oil in water emulsion

Formula W Formula VI—Sodium lauryl sulfate in a silicon oil in water emulsion

Formula X1—Sodium lauryl sulfate in a soy methyl ester oil in water emulsion

Formula X—Sodium lauryl sulfate and fatty acids in a soy methyl ester oil in water emulsion.

Thus, in these formulations, the presence or absence of the fatty acids was measured with the three solvents, silicon oil, soybean oil, and soy methyl ester, in the form of oil-in-water emulsions. The results are shown in Table 2 below.

TABLE 2

COMPARATIVE CONTROLS (SLS without Fatty Acids compared to SLS with Fatty Acids)

| | Formula V1 | Formula V | Formula W1 | Formula W | Formula X1 | Formula X |
|---|---|---|---|---|---|---|
| Formulation Description | Sodium Lauryl Sulfate in Soybean Oil in water emulsion | Sodium Lauryl Sulfate in Soybean Oil + Fatty Acids oil in | Sodium Lauryl Sulfate in Silicon oil in water emulsion | Sodium Lauryl Sulfate in Silicon oil + Fatty Acids oil in water | Sodium Lauryl Sulfate in SME in water emulsion | Sodium Lauryl Sulfate in SME + Fatty Acids oil in water |

TABLE 2-continued

COMPARATIVE CONTROLS (SLS without Fatty Acids compared to SLS with Fatty Acids)

| | Formula V1 | Formula V | Formula W1 | Formula W | Formula X1 | Formula X |
|---|---|---|---|---|---|---|
| | | water emulsion | | emulsion | | emulsion |
| Specific Formulation | SLS 5.8% in formula V1 (Soybean oil version) and V2 (Coconut Oil Version) specified in Formulation section. | SLS 5.8% See other formulants in Specific Formulation section below | SLS 5.8% in formula W1 specified in Formulation section. | SLS 5.8% See other formulants in Specific Formulation section below | SLS 5.8% in formula X1 specified in Formulation section. | SLS 5.8% See other formulants in Specific Formulation section below |
| Claims | SLS + vegetable oil (Soy and coconut tested) is effective at knocking down flying insects and limited at killing and repelling small insects. | SLS + vegetable Oil (soybean oil or Coconut Oil) + Fatty Acids is highly insecticidal with excellent KD and MT | SLS + Silicone Oil is effective at knocking down flying insects but not very effective at killing insects. Repellency is limited. | SLS + Silicone oil (DC 345) + Fatty Acids is highly insecticidal with excellent KD and MT | SLS + SME increases knock down in flying insects and kills small insects such as Ants and Aphids quickly but larger insects, arachnids and arthropods not as quick as formulas including the FAs of capric and caprylic. Highly repellent against Japanese beetles, mosquitoes, ticks and roaches. | SLS + modified fatty acid (Soy Methyl Ester) + Fatty Acids is highly repellent and insecticidal with excellent KD and MT |
| Knock Down (KD) and Mortality (MT) Efficacy Results | Small Fly KD = immed MT > 30 min | Small Fly KD = immed MT < 30 sec | Small Fly KD = immed MT > 30 min | Small Fly KD = immed MT < 30 sec | Small Fly KD = immed MT = 15 min | Small Fly KD = immed MT < 10 sec |
| | Not tested | Large Fly KD < 5 sec MT = 5 min | Not tested | Large Fly KD < 5 sec MT = 5 min | Not tested | Large Fly KD < 1 sec MT < 1 min |
| | Aphid MT > 5 sec | Aphid MT = immed | Aphid MT > 10 sec | Aphid MT = immed | Aphid MT > 5 sec | Aphid MT = immed |
| | Mosquito KD = immed MT = 10 min | Mosquito KD = immed MT = immed | Mosquito KD = immed MT > 30 min | Mosquito KD = immed MT = immed | Mosquito KD = immed MT = 4 min | Mosquito KD = immed MT = immed |
| | Not tested | Not tested | Not tested | Not tested | Not tested | Moth (1 ml) KD < 1 sec MT = 2 min |
| | Fleas KD < 1 sec MT = 10 sec Tick (2 ml) MT > 30 min | Fleas KD = immed MT = immed Tick (2 ml) MT = 4 min (and repellent on human skin) | Fleas KD < 1 sec MT = 20 sec Not Tested | Fleas KD = immed MT = immed Not tested | Fleas KD < 1 sec MT = 5 min Tick (2 ml) MT > 10 min | Fleas KD = immed MT = immed Tick (1 ml) MT < 60 sec (repellent on human skin) |
| | Nymph Roach (4 ml) MT > 30 min | Adult Roach (4 ml) MT < 30 sec Nymph Roach (2 ml) MT < 5 sec | Nymph Roach (4 ml) MT > 30 min | Adult Roach (4 ml) MT < 30 sec Nymph Roach (2 ml) MT < 5 sec | Nymph Roach (4 ml) MT = 10 min | Adult Roach (4 ml) MT < 30 sec Nymph Roach (2 ml) MT < 5 sec |
| | Ants (2 ml) MT > 10 sec Fire Ants (4 ml) MT > 30 min | Ants (1 ml) MT = immed FIRE ANTS Application rate = 2 ml | Ants (4 ml) MT > 30 sec Fire Ants (4 ml) MT > 30 min | Ants (1 ml) MT = immed FIRE ANTS Application rate = 2 ml | Ants (2 ml) MT > 5 sec Fire Ants (4 ml) MT = 10 min | Ants (1 ml) MT = immed FIRE ANTS Application |

TABLE 2-continued

COMPARATIVE CONTROLS (SLS without Fatty Acids compared to SLS with Fatty Acids)

| Formula V1 | Formula V | Formula W1 | Formula W | Formula X1 | Formula X |
|---|---|---|---|---|---|
| | MT = 30 sec | | MT = 30 sec | | Rate = 1 ml MT = 20 sec |
| Spider (8 ml) MT > 30 min | Spider (4 ml) MT < 2 min | Not tested | Not tested | Spider (8 ml) MT = 20 min | Spider (4 ml) MT < 1 min |
| Jap Beetle (4 ml) MT > 30 min (observed repellency) | Jap Beetle (4 ml) MT < 5 sec | Jap Beetle (4 ml) MT > 30 min | Jap Beetle (4 ml) MT < 5 sec | Jap Beetle (4 ml) MT = 45 sec | Jap Beetle (4 ml) MT < 5 sec |
| Not tested | Termite (1 ml) MT < 20 sec | Not tested | Termite (1 ml) MT < 20 sec | Not tested | Termite (1 ml) MT < 20 sec |
| Wasp (8 ml) KD < 5 sec MT > 30 min | Wasp (4 ml) KD < 5 sec MT = 30 sec | Wasp (8 ml) No effect | Not tested | Wasp (8 ml) KD < 1 sec MT > 30 min | Wasp (4 ml) KD < 1 sec MT = 20 sec |
| Not tested | Silver Fish (2 ml) MT < 3 sec | Not tested | Not tested | Not tested | Silver Fish (2 ml) MT < 3 sec |

Results

The results outlined in Table 2 are summarized below.

Effectiveness Against Small Flies

With respect to small flies, the data in Table 2 show that a combination of sodium lauryl sulfate and either soybean oil or silicon oil was able to immediately knock down small flies, but not kill them, even at thirty minutes post exposure. The combination of sodium lauryl sulfate and soy methyl ester was able to kill the flies, but it took fifteen minutes to do so. In contrast, when fatty acids were present, the time to mortality was under thirty seconds for the emulsions including soybean or silicon oil, and under ten seconds for the emulsions including soy methyl ester.

Effectiveness Against Large Flies

With respect to large flies, the compositions were not tested without fatty acids being present. The combination of sodium lauryl sulfate, fatty acids, and either silicon oil or soybean oil took approximately five seconds to knock down the flies, and around five minutes to kill them. In contrast, the combination of sodium lauryl sulfate, fatty acids, and soy methyl ester was able to knock down the flies in less than one second, and kill them in under one minute.

Effectiveness Against Aphids

With respect to aphids, the data in Table 2 show that a combination of sodium lauryl sulfate and either soybean oil or soy methyl ester was able to kill the aphids in around five seconds, and sodium lauryl sulfate and silicon oil was able to kill the aphids in around ten seconds. The combination of sodium lauryl sulfate, fatty acids, and any of soybean oil, silicon oil, or soy methyl ester was able to immediately kill the aphids.

Effectiveness Against Mosquitoes

With respect to mosquitoes, the data in Table 2 show that all of the formulations were able to instantly knock down the mosquitoes. The combination of sodium lauryl sulfate and soybean oil took ten minutes to kill the mosquitoes, the combination of sodium lauryl sulfate and silicon oil was did not kill the mosquitoes at thirty minutes post exposure, and the combination of sodium lauryl sulfate and soy methyl ester killed the mosquitoes within four minutes. In contrast, when fatty acids were present, the mosquitoes were instantly killed, regardless of whether the formulations included soybean oil, silicon oil, or soy methyl ester.

Effectiveness Against Moths

With respect to moths, only one formulation was tested. This formulation, a combination of sodium lauryl sulfate, fatty acids, and soy methyl ester, was able to immediately knock down the moths, and the time to mortality was around two minutes.

Effectiveness Against Fleas

With respect to fleas, the data in Table 2 show that all of the formulations knocked down the fleas, either instantaneously, or in less than one second. It took the combination of sodium lauryl sulfate and soybean oil around ten seconds to kill the fleas, the combination of sodium lauryl sulfate and silicon oil around twenty seconds to kill the fleas, and the combination of sodium lauryl sulfate and soy methyl ester around five seconds to kill the fleas. The combination of sodium lauryl sulfate, fatty acids, and any of soybean oil, silicon oil, or soy methyl ester, instantaneously killed the fleas.

Effectiveness Against Ticks

With respect to ticks, only combinations of sodium lauryl sulfate and soybean oil or soy methyl ester, with or without fatty acids, were tested. The data in Table 2 show that a combination of sodium lauryl sulfate and soybean oil was not able to kill ticks, even at thirty minutes exposure, and the combination of sodium lauryl sulfate and soy methyl ester took around ten minutes to kill the ticks. In contrast, when fatty acids were added, the combination with soybean oil took four minutes to kill the ticks, and the combination with soy methyl ester took less than one minute to kill the ticks. Further, both of the latter formulations repelled ticks from human skin.

Effectiveness Against Roaches

With respect to roaches, the data in Table 2 show that when fatty acids were not present, nymph roaches were not killed even at thirty minutes exposure to a combination of sodium lauryl sulfate and silicon oil or soybean oil, and it took ten minutes to kill roaches exposed to a combination of sodium lauryl sulfate and soy methyl ester. In contrast, when fatty acids were present, the time to mortality was under thirty seconds, regardless of whether the formulations included soybean oil, silicon oil, or soy methyl ester.

Effectiveness Against Ants

With respect to ants, the data in Table 2 show that a combination of sodium lauryl sulfate and soybean oil, silicon oil, or soy methyl ester was able to kill the ants in around ten, thirty, and five seconds, respectively. In contrast, when fatty acids were present, the ants were instantly killed, regardless of whether the formulations included soybean oil, silicon oil, or soy methyl ester.

With respect to fire ants, the data in Table 2 show that a combination of sodium lauryl sulfate and either soybean oil or silicon oil was unable to kill fire ants, even at thirty minutes post exposure. The combination of sodium lauryl sulfate and soy methyl ester was able to kill the fire ants, but took ten minutes to do so. In contrast, when fatty acids were present, the time to mortality was around thirty seconds for the emulsions including soybean oil or silicon oil, and under twenty seconds for the emulsions including soy methyl ester.

Effectiveness Against Spiders

With respect to spiders, only formulations including soybean oil and soy methyl ester were tested. The data in Table 2 show that a combination of sodium lauryl sulfate and soybean oil was unable to kill spiders, even at thirty minutes post exposure. The combination of sodium lauryl sulfate and soy methyl ester was able to kill the spiders, but it took twenty minutes to do so. In contrast, when fatty acids were present, the time to mortality was under two minutes for the emulsions including soybean oil, and under one minute for the emulsions including soy methyl ester.

Effectiveness Against Japanese Beetles

With respect to Japanese beetles, the data in Table 2 show that a combination of sodium lauryl sulfate and either soybean oil or silicon oil was unable to kill them, even at thirty minutes post exposure. The combination of sodium lauryl sulfate and soy methyl ester was able to kill the Japanese beetles in around forty five seconds. In contrast, when fatty acids were present, all formulations killed the Japanese beetles in less than five seconds.

Effectiveness Against Termites

With respect to termites, only formulations including fatty acids were tested. The data in Table 2 show that all formulations killed the termites in less than twenty seconds.

Effectiveness Against Wasps

With respect to wasps, the data in Table 2 show that a combination of sodium lauryl sulfate and either soybean oil or soy methyl ester was able to immediately knock down the wasps. However, the combination of sodium lauryl sulfate and silicon oil was not able to knock down the wasps. Accordingly, the formulation with sodium lauryl sulfate, silicon oil, and fatty acids was not evaluated.

The combination of sodium lauryl sulfate and either soybean oil or soy methyl ester was unable to kill the wasps, even at thirty minutes exposure. In contrast, when fatty acids were present, the emulsion including soybean oil killed the wasps in thirty seconds, and the emulsion including soy methyl ester killed the wasps in twenty seconds.

Effectiveness Against Silver Fish

Only two of the formulations were tested on silver fish, the formulations with sodium lauryl sulfate, fatty acids, and either soybean oil or soy methyl ester. The data in Table 2 show that both of these formulations killed the silver fish in less than three seconds.

Conclusions

The combination of sodium lauryl sulfate and vegetable oil (for example, coconut and soybean oils) is effective at knocking down flying insects, but limited in its ability to kill or repel small insects.

The combination of sodium lauryl sulfate, vegetable oil (for example, coconut and soybean oils) and $C_{6-12}$ fatty acids is highly insecticidal, with excellent knock down and time to mortality.

The combination of sodium lauryl sulfate and silicon oil is effective at knocking down flying insects, but not very effective at killing insects. Repellency is limited. In contrast, the combination of sodium lauryl sulfate, silicon oil, and $C_{6-12}$ fatty acids is highly insecticidal, with excellent knock down and time to mortality.

The combination of sodium lauryl sulfate and soy methyl ester is more effective at knocking down flying insects than the combination of sodium lauryl sulfate and either soybean oil or silicon oil, and is able to quickly kill small insects such as ants and aphids. However, the combination required significantly more time to kill larger insects, arachnids, and arthropods than a comparable formula that included capric and/or caprylic acid. When these fatty acids were present, the composition was highly repellent and insecticidal, with excellent knockdown and time to mortality.

EXAMPLE 3

Animal/Cattle Test

During the summer on a cattle ranch in Fayetteville, Ark., Formula X was applied on show cattle prior to them going to the Arkansas State Fair. Even in the show barns, there were no flies on the cattle, even though they were abundant in the barns and arena.

Again, the product was applied two weeks later to a number of herd used in the health program. The veterinarian normally applies Pymectrin as part of the health program. Formula X was applied to 25 head and the results for a two week period, including two small rain showers, were equal to or better than the veterinarian-applied Permectrin.

EXAMPLE 4

Testing and Results for Repellant Properties and a Comparison of Pesticidal Properties vs. RAID™

Repellent Properties:

It was observed (as shown in Table 1, above) that compositions including sodium lauryl sulfate, fatty acids and soy methyl ester were highly repellent in addition to being highly insecticidal. The compositions including sodium lauryl sulfate, soy methyl ester, and undecanone were also highly repellent in addition to being highly insecticidal.

With respect to ticks, sodium lauryl sulfate was not observed to be particularly repellent on its own. In contrast, when fatty acids were added, alone or in combination with soybean oil or soy methyl ester, the compositions were repellent when applied to human skin. Similarly, compositions including sodium lauryl sulfate and undecanone were repellent to ticks when the compositions were applied to human skin.

Pesticidal Comparison with RAID®

Active: Tetramethrin 0.35%, Permethrin 0.10%, dcis/trans Allethrin 0.10%

The pesticidal effectiveness of Raid® Flying Insect Killer Formula 6 (SC Johnson) was compared to Formula X. Raid had no effect when sprayed on Japanese Beetles. RAID knocked down small flying insects such as flies and mosquitoes, but took longer than 5 minutes to kill these insects.

RAID was ineffective against Ticks, Wasps and Carpenter bees. In contrast, 2 ml of Formula X killed Japanese beetles, flies, mosquitoes, ticks in less than 1 minute and 4 ml killed wasps and Carpenter bees within 5 minutes.

EXAMPLE 5

Field Evaluation of the Efficacy of Two Formulations Against Moisture Ants

An evaluation of the efficacy of two of the formulations described herein at controlling moisture ants was conducted in southern Ontario.

The purpose of this study was to assess, under field conditions, the efficacy of the following formulations, with and without an enzyme added, to control moisture ants (*Lasius pallitarsis*). Moisture ants can be found making small mounds of excavated soil in lawns and laneways similar to the more familiar pavement ants.

Formulation
3% Sodium Lauryl Sulfate
1% Lauric Acid
2.5% Potassium Oleate
4% Glycerin
2% Glycerol Monostearate
87.5% Water
(Optionally including an enzyme)

The enzyme is the enzyme registered under Chemical Abstracts No. [CAS 9014-01-1]. Also suitable for use is the enzyme mixture known as "Bacto-Zyme," produced by International Enzymes, Inc. of Las Vegas, Nev., as well as the various protease enzymes described herein. The enzyme was present in a concentration of about 2.0% to about 10% by weight of the composition.

Materials and Methods

Site

The study was conducted utilizing a grass lawn and unpaved laneway. The study area bordered a large mixed deciduous/coniferous woodlot (e.g. maples, poplars, birch, tamarack, white cedar, and white pine are predominant species) with secondary growth under the canopy in a rural area four km south of the southern city limit of Guelph, Ontario. Adjacent to the study area was a cattail marsh (>four hectares) approximately 30 meters from the center of the study area.

Ant Nests

Prior to the start of the test, ant nests were located at the study site. Each nest was marked with a numbered stake and ants were collected from each nest. Ants were frozen and subsequently identified. The test proceeded when 15 nests were located and colony activity was later confirmed. Nests were at least 2 m apart but were typically 3-6 m apart.

Experimental Design

The test consisted of one trial with 15 nests of the ant *Lasius pallitarsis*, the moisture ant. The trial consisted of ten treated nests (five per product) and five non-treated control nests. Treatments were assigned randomly. Treatments and nests were designated as:

T1=nests T1-1 through T1-5
T2=nests T2-1 through T2-5
T3=nests T3-1 through T3-5
First number=treatment
Last number=rep
Treatment 1=Control
Treatment 2=Formulation without added enzyme
Treatment 3=Formulation with added enzyme Observations The study took place from Aug. 26 to Sep. 3, 2009. Observations were made one day prior to treatment, the day of treatment (before treatment) and one, two, three, and seven days post-treatment. Observations were made once a day. Time of observations was dependent on weather. On hot sunny days, ant activity was very low or non-existent mid-day so observations were made early evening, 1800-1900 h. On overcast cooler days observations were made afternoons, 1200-1600 h to ensure presence of ant activity which could be otherwise lower if evenings were cool. Presence or forecast of rain also influenced observation times.

An observation consisted of a 2-minute count per nest. The number of ants entering and leaving the nest was counted or estimated and at the end of the 2-minute count, activity was also rated on a scale of 0-5. The rating scale used was as follows:

0 ants=0
21-50 ants=3
1-5 ants=1
51-75 ants=4
6-20 ants=2
>76 ants=5

Temperature and general weather conditions (wind, cloud cover, precipitation) were monitored at each observation time. At the conclusion of the trials two treated nests (one per product) and one control nest from each trial was excavated. The number of live ants was recorded.

Treatment

Treatments took place from 1900-2000 h on Aug. 27, 2009. Both products were poured into graduated hand mister bottles. To record the volume applied, the volume was recorded before and after each treatment. The amount applied was relative to the size of the nest. A treatment was determined to be complete when the nest was saturated. The mean amount applied to moisture ant nests was 44.5±7.4 ml.

Data Analysis

The mean number of ants observed at treated and non-treated nests was compared using analysis of variance and a Duncan's Multiple Range Test. Differences in the mean ant activity rating were determined non-parametrically using the Kruskal-Wallis analysis of variance and the Mann-Witney-Wilcoxon comparison of means. Data were analysed separately for each day of observation and pre-treatment and post-treatment days combined. The analyses were completed using Statistical Analysis Systems version 6.12 (SAS Institute Inc., Cary, N.C.).

Results

Pre-treatment counts demonstrated that all nests had similar levels of activity and were not statistically different. Where the formulation did not include any added enzyme, it provided approximately 94% control of moisture ants throughout the post-treatment observation period. Where the formulation included the added enzyme, it provided approximately 98% control of moisture ants throughout the post-treatment observation period. There was no statistical difference in the performance of the two products. For both products, differences in ant activity between treated and non-treated nests were statistically different post-treatment ($P<0.05$).

The mean temperature during observations was 20.2° C. (range=16.0, 24.0). There was a single rain event on the night of August 28/29. Before the rain event, the nests were covered with a metal hoop and plastic bag to keep the nests dry overnight. Bags were removed the next morning.

At the conclusion of the trial, three nests were dug up (one per treatment) and live ants were counted. For the nest treated with the formulation without added enzyme, zero ants were found. For the nest treated with the formulation, with added enzyme, 10 ants were found. Upon examination of the control nest, 108 ants were counted.

TABLE 1

Mean number[1,2] (± one standard deviation) of ants observed in field tests conducted near Guelph, Ontario, 2009, before and after treatment with two HOMS products.

| Day | Control | Formulation Without Enzyme | Formulation With Enzyme |
|---|---|---|---|
| −1 | 21.2 ± 6.2 a | 16.0 ± 5.7 a | 17.6 ± 5.4 a |
| 0 | 16.4 ± 4.2 a | 15.6 ± 3.0 a | 19.0 ± 4.2 a |
| 1 | 18.6 ± 5.2 a | 0 b | 0.4 ± 0.4 b |
| 2 | 20.2 ± 4.9 a | 1.0 ± 0.6 b | 0.4 ± 0.2 b |
| 3 | 18.6 ± 2.6 a | 1.2 ± 1.0 b | 0.4 ± 0.2 b |
| 7 | 40.4 ± 8.4 a | 3.6 ± 2.1 b | 0.4 ± 0.2 b |
| Days pre-treatment | 18.8 ± 3.6 a | 15.8 ± 3.0 a | 18.3 ± 3.2 a |
| Days post-treatment | 24.5 ± 3.4 a | 1.5 ± 0.6 b | 0.4 ± 0.1 b |

[1] Values followed by different letters in the same row are significantly different (P < 0.05).
[2] Number of repetitions equalled five.

TABLE 2

Mean activity rating[1,2] (± one standard deviation) of ants observed in field tests conducted near Guelph, Ontario, 2009, before and after treatment with two HOMS products.

| Day | Control | Formulation Without Enzyme | Formulation With Enzyme |
|---|---|---|---|
| −1 | 2.4 ± 0.2 a | 2.2 ± 0.2 a | 2.4 ± 0.2 a |
| 0 | 2.4 ± 0.2 a | 2.2 ± 0.2 a | 2.4 ± 0.2 a |
| 1 | 2.4 ± 0.2 a | 0 b | 0.2 ± 0.2 b |
| 2 | 2.4 ± 0.2 a | 0.4 ± 0.2 b | 0.4 ± 0.2 b |
| 3 | 2.2 ± 0.2 a | 0.4 ± 0.2 b | 0.4 ± 0.2 b |
| 7 | 3.2 ± 0.4 a | 0.8 ± 0.4 b | 0.4 ± 0.2 b |
| Days pre-treatment | 2.4 ± 0.2 a | 2.2 ± 0.1 a | 2.4 ± 0.2 a |
| Days post-treatment | 2.6 ± 0.2 a | 0.4 ± 0.1 b | 0.4 ± 0.1 b |

[1] Values followed by different letters in the same row are significantly different (P < 0.05).
[2] Number of repetitions equalled five.

Conclusions

The two formulations, one with an enzyme, and one without, provided excellent control of moisture ants (*Lasius pallitarsis*) in a field test in southern Ontario, Canada. The formulation without added enzyme provided approximately 94% control of moisture ants throughout the post-treatment observation period. The formulation with added enzyme provided approximately 98% control of moisture ants throughout the post-treatment observation period. There was no statistical difference in the performance of the two products.

EXAMPLE 5

Phytotoxicity Testing

The following formulation was tested for phytotoxicity.
Formulation
3% Sodium Lauryl Sulfate
1% Lauric Acid
2.5% Potassium Oleate
4% Glycerin
2% Glycerol Monostearate
87.5% Water
(Optionally including an enzyme)

The formulation was applied at a concentration of approximately 1 oz per square foot by spray application on the following vegetation. There was no observed degradation of the vegetation after spraying and for each week of observation over a 6 week period after spraying.

Dandelion
Ivy
Rye grass
Fescue grass
Flowers including roses, hyacinth, gladiolas, hydrangea, azalea, rhododendron and other ornamentals
Tomato plants
Squash plants
Carrot plants
Bean plants
Okra plants
Corn plants
Cucumber plants
Gardenia bushes
Crepe myrtle tree
Peach tree This composition, and other compositions which, according to the protocol identified above are non-phytotoxic or substantially non-phytotoxic, can be safely administered, such as by spray administration, to vegetation, lawns and gardens.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method of combating pests, at a locus containing or susceptible to the presence of same, said method comprising applying to at least a portion of said locus a pest combatting composition, in the form of an oil-in-water emulsion, a water-in-oil emulsion, a micelle formulation, or an aerosol formulation, comprising an effective, pest-combatting amount of sodium lauryl sulfate and one or more $C_{6-12}$ fatty acids and wherein said pests comprise a pest selected from the group consisting of bed bugs, flies, mosquitoes, wasps, ants, ticks, fleas, cockroaches, silver fish, thrips, gnats, chiggers, aphids, Japanese beetles, mites, potato beetles, bean beetles, flea beetles, fleahoppers, squash bugs, slugs, leaf hoppers, harlequin bugs, milk weed bugs, spiders, lice, rodents, and deer,
wherein the fatty acids comprise one or more of lauric, capric or caprylic acid.

2. The method of claim 1, wherein the pest is an ant, and the composition is applied in the form of a drench.

3. The method of claim 1,
wherein the formulation further comprises an enzyme, and the enzyme is a protease or helps to control allergens contributed by pests.

4. The method of claim 1, wherein the amount of sodium lauryl sulfate in the pest-combatting composition is between about 0.1 and about 10 percent by weight of the composition.

5. The method of claim 1, wherein the composition further comprises soy methyl ester.

6. The method of claim 1, wherein the composition further comprises 2-undecanone or rue oil.

7. The method of claim 1, wherein the composition further comprises a carrier oil, an essential oil, or a botanical extract.

8. The method of claim 7, wherein the carrier oil is silicon oil or a vegetable oil.

9. A method of combating pests, at a locus containing or susceptible to the presence of same, said method comprising applying to at least a portion of said locus a pest combatting composition, in the form of an oil-in-water emulsion, a water-in-oil emulsion, a micelle formulation, or an aerosol formulation, comprising an effective, pest-combatting amount of an essential oil, sodium lauryl sulfate and one or more $C_{6-12}$ fatty acids, wherein the essential oil is selected from the group consisting of peppermint oil, menthol, citral, lemongrass oil, and cedar oil wherein the fatty acids comprise one or more of lauric, capric or caprylic acid and wherein said pests comprise a pest selected from the group consisting of bed bugs, flies, mosquitoes, wasps, ants, ticks, fleas, cockroaches, silver fish, thrips, gnats, chiggers, aphids, Japanese beetles, mites, potato beetles, bean beetles, flea beetles, fleahoppers, squash bugs, slugs, leaf hoppers, harlequin bugs, milk weed bugs, spiders, lice, rodents, and deer.

10. The method of claim 1, wherein the composition is in the form of a lotion, spray, crème, or aerosol.

11. The method of claim 1, wherein the composition further comprises at least one additional active or inactive ingredient.

12. The method of claim 11, wherein the at least one additional active or inactive ingredient comprises an ingredient selected from the group consisting of additional pest-combating ingredients.

13. The method of claim 11, wherein the composition comprises an ingredient selected from the group consisting of pest repellents and cidal agents.

14. The method of claim 1, wherein the composition further comprises a second insect repellent or cidal ingredient.

15. The method of claim 1, wherein the composition further comprises a sticking agent or a thixotropic agent.

16. The method of claim 1, wherein the locus is or comprises domestic or industrial premises.

17. The method of claim 16, wherein the domestic premises comprises furniture.

* * * * *

UNITED STATES PATENT AND TRADEMARK OFFICE
CERTIFICATE OF CORRECTION

| | | |
|---|---|---|
| PATENT NO. | : 8,834,908 B2 | Page 1 of 1 |
| APPLICATION NO. | : 13/402248 | |
| DATED | : September 16, 2014 | |
| INVENTOR(S) | : Jones | |

It is certified that error appears in the above-identified patent and that said Letters Patent is hereby corrected as shown below:

In the Specification

Column 3, line 6: "mono-glycerides" should be -- monoglycerides --.

Column 10, lines 43-44: "bistrif-louron" should be -- bistrifluron --.

Column 11, line 38: "nornicotine" should be -- nomicotine --.

Signed and Sealed this
Eighteenth Day of November, 2014

Michelle K. Lee
*Deputy Director of the United States Patent and Trademark Office*